United States Patent
Welt et al.

(10) Patent No.: US 6,190,640 B1
(45) Date of Patent: *Feb. 20, 2001

(54) METHOD FOR TREATING NEOPLASIA USING HUMANIZED ANTIBODIES WHICH BIND TO ANTIGEN A33

(75) Inventors: Sydney Welt; Gerd Ritter; Leonard Cohen; Clarence Williams, Jr.; Elizabeth Carswell Richards; Mary John; Lloyd J. Old, all of New York, NY (US)

(73) Assignees: Ludwig Institute for Cancer Research, London (GB); Sloan-Kettering Institute for Cancer Research, NY (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/752,693

(22) Filed: Nov. 19, 1996

Related U.S. Application Data

(63) Continuation of application No. PCT/US96/07321, filed on May 21, 1996, which is a continuation-in-part of application No. 08/020,223, filed on Feb. 16, 1993, now Pat. No. 5,431,897, which is a continuation of application No. 07/673,153, filed on Mar. 18, 1991, now abandoned, which is a continuation of application No. 07/327,765, filed on Mar. 23, 1989, now abandoned, which is a continuation-in-part of application No. 07/118,411, filed on Nov. 6, 1987, now abandoned, which is a continuation of application No. 06/724,991, filed on Apr. 19, 1985, now abandoned.

(51) Int. Cl.[7] .......................... A61K 51/00; A61K 49/00; A61K 35/14

(52) U.S. Cl. .................. 424/1.49; 424/1.69; 424/130.1; 424/155.1; 424/133.1; 424/138.1; 424/141.1; 424/152.1; 424/156.1; 424/172.1; 424/174.1

(58) Field of Search .................... 424/1.85, 1.49, 424/1.69, 130.1, 155.1, 133.1, 138.1, 141.1, 152.1, 156.1, 172.1, 174.1

(56) References Cited

U.S. PATENT DOCUMENTS

| | | | | |
|---|---|---|---|---|
| 5,643,550 | * | 7/1997 | Welt et al. | 424/1.85 |
| 5,776,456 | * | 7/1998 | Anderson et al. | . |
| 5,968,770 | * | 10/1999 | Falb et al. | . |

FOREIGN PATENT DOCUMENTS

94/13805 * 6/1994 (WO).

OTHER PUBLICATIONS

Gavin –Chesa et al (Intl, J. Oncol. 9/3 465–471, 1996.*

Bennet, (Neurotranmitter Receptor Binding, Yamamura et al, eds Raven Press, NY p. 59, 1978.*

Welt et al (Proc. An Meet, AM. Soc. Clin. Oncol, 11: A489, 1992.*

* cited by examiner

*Primary Examiner*—Susan Ungar
(74) *Attorney, Agent, or Firm*—Fulbright & Jaworiski, LLP

(57) ABSTRACT

The invention involves the therapeutic use of humanized antibodies, fragments, etc., which bind to the antigen A33. These antibody molecules are useful in the treatment of various neoplasias, including colon cancer. Various modes of administration, and doses are described.

6 Claims, 12 Drawing Sheets

FIG. 5A

| | |
|---|---|
| mA33 | DIVMTQSQKFMSTSVGDRVSITCKASQNVRTVVAWYQQKPGQSPK |
| hA33 | DIQMTQSPSSLSVSVGDRVTITCKASQNVRTVVAWYQQKPGLAPK |
| mA33 | TLIYLASNRHTGVPDRFTGSGSGTDFTLTISNVQSEDLADYFCLQHWSYP |
| hA33 | TLIYLASNRHTGVPSRFSGSGSGTDFTFTISSLQPEDIATYFCQQHWSYP |
| mA33 | LTFGSGTKLEVKR |
| hA33 | LTFGQGTKVEVKR |

FIG. 5B

| | |
|---|---|
| mA33 | EVKLVESGGG LVKPGGSLKL SCAASGFAFS TYDMSWVRQT PEKRLEWVAT |
| hA33 | EVQLLESGGG LVQPGGSLRL SCAASGFAFS TYDMSWVRQA PGKGLEWVAT |
| mA33 | ISSGGSYTYYLDSVKGRFTISRDSARNTLYLQMSSLRSED TALYYCAPTT |
| hA33 | ISSGGSYTYYLDSVKGRFTISRDSSKNTLYLQMNSLQAED SAIYYCAPTT |
| mA33 | VVPFAYWGQGTLVTVSA |
| hA33 | VVPFAYWGQGTLVTVSS |

1 2 3 4

1 2 3 4

METHOD FOR TREATING NEOPLASIA USING HUMANIZED ANTIBODIES WHICH BIND TO ANTIGEN A33

RELATED APPLICATIONS

This application is a continuation in part of International Application PCT/US96/07321, filed on May 21, 1996, designating the United States, which is a continuation in part of U.S. patent application Ser. No. 08/020,223 filed Feb. 16, 1993, now U.S. Pat. No. 5,431,897; which is a Continuation Application of U.S. patent application Ser. No. 07/673,153 filed Mar. 18, 1991, now abandoned; which is a Continuation Application of U.S. patent application Ser. No. 07/327,765 filed Mar. 23, 1989, now abandoned; which is a Continuation-In-Part Application of U.S. patent application Ser. No. 07/118,411 filed Nov. 6, 1987, now abandoned; which is a Continuation Application of U.S. patent application Ser. No. 06/724,991 filed Apr. 19, 1985,now abandoned. All of these applications are incorporated by reference.

FIELD OF THE INVENTION

This invention relates to a method of reducing the effects of colon cancer tumors, utilizing at least one monoclonal antibody. Specifically, at least one monoclonal antibody is utilized in conjunction with an anti-tumor drug, a peptide which inhibits DNA tumor activity or a radioisotope in the treatment of colorectal carcinoma. This invention further relates to a method of delivering genetic material to DNA of tumor cells and to a method of delivering anti-cancer agents to nuclei of colon tumor cells, as well as to monoclonal antibodies which are specific for A33 antigen; an antigen found on colon cancer cells.

BACKGROUND OF THE INVENTION

Colorectal carcinoma is a malignant neoplastic disease. There is a high incidence of colorectal carcinoma in the Western world, particularly in the United States. Tumors of this type often metastasize through lymphatic and vascular channels. Many patients with colorectal carcinoma eventually die from this disease. In fact, it is estimated that 62,000 persons in the United States alone die of colorectal carcinoma annually.

To date, systemic therapies and chemotherapies have been developed for the treatment of colorectal cancer. However, no therapies have exhibited sufficient anti-tumor activity to prolong the survival of colorectal carcinoma patients with metastatic disease with any degree of reliability. As a result, a need still exists to develop methods for the successful treatment of colorectal carcinoma.

It is therefore an object of this invention to provide methods for reducing the effects of colon cancers.

It is another object of this invention to provide a method of delivering genetic material to DNA of colon cancer cells.

It is a further object of this invention to provide a method of delivering anti-cancer agents to nuclei of colon cancer cells.

It is a still further object of this invention to provide antibodies, including monoclonal antibodies, humanized antibodies, chimeric antibodies, trimeric antibodies, heteromeric antibodies and single chain antibodies which are useful in the treatment of colon cancer.

SUMMARY OF THE INVENTION

This invention is directed to methods of reducing the effects of colon cancer comprising the administration of tumor-associated antibody conjugates. Specifically, at least one conjugate of an antibody which is associated with colon cancer cells and an anti-cancer drug is administered. Alternatively, at least one conjugate of an antibody which is specific for colon cancer cells and a peptide which inhibits DNA activity of said cells is administered in a pharmaceutically effective amount so as to reduce the effects of colon cancer. Another method of reducing the effects of colon cancer comprises administering a pharmaceutically effective amount of at least one conjugate of an antibody which is specific for said tumor and a radioisotope.

This invention is further directed to a method of delivering genetic material to colon cancer cells comprising contacting tumor cells with genetic material conjugated to an antibody which is internalized into the tumor cells, thereby mediating integration of genetic material into DNA.

In addition, anti-cancer agents can be delivered to the nuclei (DNA) of colon cancer cells by contacting the cells with an anti-cancer agent conjugated to an antibody which is internalized into said cells.

This invention is also directed to antibodies, including monoclonal, humanized, chimeric, trimeric, heteromeric and single chain antibodies, which can be utilized to reduce the effects of colon cancers.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 5a represents the light chain of the murine A33 antibody (mA33, SEQ ID NO1) and the light chain of the humanized murin A33 antibody (hA33, SEQ ID NO:2). FIG. 5b represents the heavy chain of the murine A33 antibody (mA33, SEQ ID NO3) and the heavy chain of the humanized murine A33 antibody (hA33, SEQ ID NO:4).

DETAILED DESCRIPTION OF THE INVENTION

Figure 1:
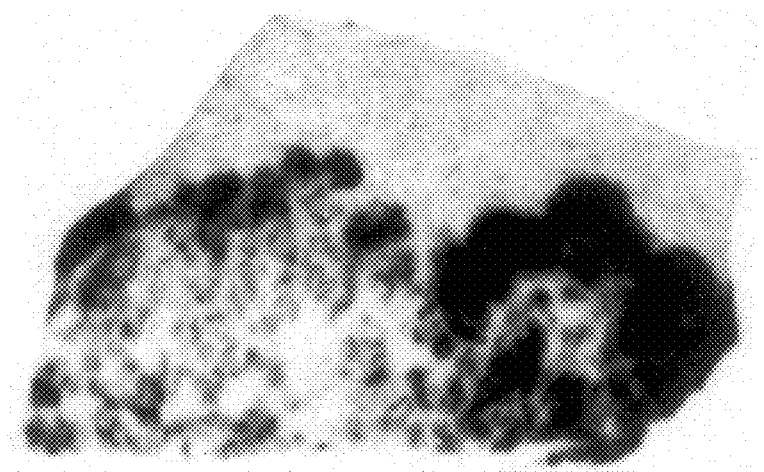
FIG. 1 is an autoradiograph which shows the accumulation of $^{131}$-mAb A33 in hepatic lesions but not in surrounding normal liver tissue.

Murine monoclonal antibody A33, (referred to herein as mAb A33) is a monoclonal antibody of the IgG2a isotype which defines a cell-surface antigen referred to as antigen A33, which is present on greater than 95% of colorectal carcinomas and in normal intestinal mucosa (see Table 1). Among colorectal carcinomas, A33 antigen is expressed with a homogeneous cell surface distribution in greater than 95% of antigen-positive lesions. Moreover, A33 antigen is found in colon cancers regardless of their degree of histologic differentiation and in primary as well as metastatic lesions, including liver metastases.

TABLE 1

Immunohistochemical Analysis of A33 Antigen Expression in Human Tumors

| Tumor Type | A33-positive No. Cases | % positive cells | |
|---|---|---|---|
| Carcinomas | | | |
| Colorectal carcinoma | | | |
| primary tumors | 45/47 | 75–100 | n = 40 |
| | | 25–50 | n = 5 |
| metastases | 23/25 | 75–100 | n = 22 |
| | | 25–50 | n = 1 |
| Gastric carcinoma | 14/30 | | |
| signet ring type | 12/12 | 75–100 | n = 12 |
| Esophageal carcinoma | 2/8 | | |
| intestinal type | 1/1 | | |
| mucinous type | 1/1 | | |
| Pancreatic carcinoma | 0/8 | | |
| Lung carcinoma | 0/16 | | |
| Breast carcinoma | 0/19 | | |
| Renal carcinoma | 0/16 | | |
| Bladder carcinoma | 0/19 | | |
| Prostate carcinoma | 0/4 | | |
| Testicular carcinoma | 0/4 | | |
| Ovarian carcinoma | 1/56 | | |
| Endometrial carcinoma | 1/4 | | |
| Thyroid carcinoma | 0/4 | | |
| Liver carcinoma | 0/2 | | |
| Larynx carcinoma | 0/2 | | |
| Mesothelioma | 1/7 | | |
| Neuroendocrine carcinomas | 0/8 | | |
| Neuroectodermal tumors | | | |
| Melanoma | 1/10 | | |
| Gliomas | 0/8 | | |
| Neuroblastomas, Glgnb | 0/10 | | |
| Sarcomas | | | |
| Leiomyosarcoma | 0/7 | | |
| MFII | 0/5 | | |
| Fibrosarcoma | 0/3 | | |
| Liposarcoma | 0/6 | | |
| MPNT | 0/6 | | |
| Chondrosarcoma | 0/14 | | |
| Others | 0/9 | | |
| Lymphomas | 0/12 | | |

Antigen A33 has not been detected in the sera of patients with antigen A33-positive colon cancers, in the tumoral secretions of mucinous colon cancers, nor in the supernatant of antigen A33-positive colon cancer cell lines. This suggests that antigen A33 is not a secreted molecule. In the normal gastrointestinal tract, antigen A33 is found in normal small and large intestinal mucosa, showing a uniform cell surface distribution throughout the crypts. A detailed survey of antigen A33 expression in greater than 300 tumors of diverse histologic types and in normal human adult and fetal tissues has shown the restricted distribution pattern of this antigen. As discussed hereinbelow, the inventors have found that among neoplastic tissues, antigen A33 is present in colon cancers and in a subset of gastric cancers showing intestinal metaplasia, but not in any of the other epithelial cancers tested. Antigen A33 was not found to be present in sarcomas, neuroectodermal tumors, or lymphoid neoplasms. These tissues were consistently found to be antigen A33-negative.

As disclosed in U.S. Pat. No. 5,160,723, the entirety of which is incorporated herein by reference, monoclonal antibody A33 is specific for antigen A33 found on colon cancer cell surfaces, and is therefore specific for colon cancer. As a result, monoclonal antibody A33, and other antibodies which are antigen A33-specific, can be used for colon cancer diagnosis. The antibodies can be conjugated with anticancer agents, peptides or radioisotopes and utilized for colon tumor treatment.

EXAMPLE I

Internalization of $^{125}$I-mAb A33 in Heterotransplanted Human Colon Tumors in Mice The A33 antigen has several features which make it useful for immunotherapy studies. It is present in more than 95% of colorectal cancers, including primary and metastatic lesions. It is homogeneously expressed in tumor nodules, and it is not secreted into the blood stream. Further, clinical evaluation of $^{131}$I and $^{125}$I-mAb A33 have shown exceptionally good targeting to metastatic colon cancer sites and evidence for clinical responses with only limited toxicity. Biopsy-based quantitative dosimetry data for mAb A33 show that mAb A33 can be used for effective and safe radioimmunotherapy.

Monoclonal antibody A33 was radiolabelled with $^{125}$I by procedures described in U.S. Pat. No. 5,160,723 (the '723 Patent). The $^{125}$I-labelled A33 monoclonal antibody is referred to herein as $^{125}$I-mAb A33. $^{125}$I-mAb A33 was administered to nu/nu mice which were heterotransplanted with human colon tumors. The mice were subsequently studied for $^{125}$I-mAb A33 localization. Parameters of radiolabelled monoclonal antibody A33 localization were evaluated in nu/nu mice using the A33-positive colon carcinoma cell line SW1222. This model is of special interest because much is known about the kinetics and trafficking of mAb A33 in cultured SW1222 cells in vitro. Specifically, it is known that mAb A33 is rapidly internalized into SW1222 cells (approximately 33% in less than 1 hour); that the pathway of mAb A33 internalization is via macropinosomes generated from cell membrane ruffling; that on average, SW1222 cells bind 800,000 molecules of mAb A33 per cell; that the t½ of $^{125}$I-mAb A33 retention by these cells is 12–14 hours; and that most of the internalized mAb A33 is released in intact immunoreactive form. The released mAb A33 is capable of rebinding to tumor cells, resulting in higher uptake/retention of this monoclonal antibody. This occurs in both mice and humans (human data described hereinbelow).

The peak tumor uptake for $^{125}$I-mAb A33 at 24–48 hours after injection was 35–40% injected dose/g. Tumor:liver ratios ranged from 30:1 to 40:1, and tumor:blood ratios ranged from 10:1 to 15:1. These values showed some minor variation depending on the dose of monoclonal antibody administered, and localization parameters were found to be antigen-specific as tumor uptake could be blocked by the intravenous administration of excess unlabelled mAb A33, but not with unrelated negative control mAb.

$^{125}$I-mAb A33 was cleared from tumor xenografts with a t½ of 60 hours. In contrast, mAb A33 radiolabelled with $^{111}$In showed localization of 45% injected dose/g tumor, and retention of the isotope was significantly longer (greater than 7 days). This was most likely due to cytoplasmic trapping of $^{111}$In. This in vivo model of mAb A33 localization to tumor is of great value in evaluating the relative effectiveness of various antibody conjugates, and for dosimetry calculations involving a variety of isotopes.

EXAMPLE II

Internalization of $^{125}$I-mAb A33 in Humans with Colon Cancer

The A33 antigenic system can be used for immunotherapy. It is particularly suitable for this use since there is rapid internalization of antigen A33-mAb A33 complexes into colon cancer cells. Further, mAb A33 conjugates, which have intracellular sites of action, have the ability to kill colon cancer cells in vitro and in vivo.

The inventors studied the localization and cytotoxic effects of $^{125}$I-labelled mAb A33 in humans. $^{125}$I radionuclide exerts its cytotoxic effects primarily through short-range Auger electrons, which are most effective when generated in close proximity (<1–4 µm) to the cell nucleus. Accordingly, one of the expected benefits of $^{125}$I-mAb A33 compared to $^{131}$I-mAb A33 is reduced bone marrow toxicity. With patients who were treated with $^{125}$I-mAb A33 at an initial dose of 50 mCi/m$^2$, no toxicity was observed. Tumor imaging by external $^{125}$I scanning with a collimator was achieved in all patients, and positive tumor images were followed for up to 35 days after antibody infusion. This result was surprising since only a small fraction of $^{125}$I radiation was previously considered to be suitable for scanning.

Most of the $^{125}$I radiation acts at very short range, and the positive images suggest significant tumor doses. Of the first nine patients, one showed a response with 35% reduction in carcinoembryonic antigen (CEA) levels at 4 weeks after treatment. It was not possible to evaluate one patient as this patient had a pulmonary lesion resection. Tumor regression resulted from $^{125}$I-mAb A33 administration. In addition, patients who did not respond to chemotherapy prior to being administered $^{125}$I-mAb A33 were responsive to chemotherapy (i.e., had tumor regression) after $^{125}$I-mAb A33 administration. Therefore, the antibody-radioisotope conjugates of the invention can be used to sensitize patients to chemotherapy.

EXAMPLE III

Biodistribution of $^{131}$I-mAb A33 in Humans with Colon Cancer

The biodistribution of $^{131}$I labelled mAb A33 in presurgical patients with suspected hepatic metastases of colorectal cancer was studied. This was done in order to establish the targeting potential of mAb A33 as determined by external scanning techniques and biopsy-based dosimetry, and to show that mAb A33 targeting is antigen-specific when compared to an unrelated isotype-matched negative control mAb, mAb TA99.

Efficient and consistent radiolabelling of mAbs with retention of optimal levels of immunoreactivity is essential for radioimmunotherapy. Preclinical evaluation showed that mAb A33 labelled with up to 50 mCi $^{131}$I/mg protein retained 40–70% of the original immunoreactivity as determined by sequential absorption analysis. Fifty-one doses of mAb A33 were labelled in 42 iodination procedures, using a protocol designed to achieve a specific activity of about 15 mCi/mg (actual range 12.5 to 22 mCi/mg). Seventeen patients received samples with 40–70% immunoreactivity. Six patients received some preparations of $^{131}$I-mAb A33 at 40–70% immunoreactivity and some with 20–35% immunoreactivity, which is considered to be suboptimal.

Seventeen patients were administered $^{131}$I-mAb A33 at five dose levels (0.2–50 mg) and three patients received the unrelated isotype-matched negative control $^{131}$I-mAb TA99 (2 mg) together with $^{125}$I-mAb A33 (2 mg). Following infusion over a 1-hour period, peak serum levels of $^{131}$I-mAb A33 and control $^{131}$I-mAb TA99 reached 28% ID/l at all dose levels tested, consistent with free distribution in the intravascular plasma volume (median 2.57 l) as determined from $^{99m}$Tc-HSA serum studies in the same patients. Clearance of $^{131}$I-mAb A33 from the blood showed that the half-life of $^{131}$I-mAb A33 was found to decrease more rapidly than the levels of negative control $^{131}$I-mAb TA99, most likely due to in vivo absorption of $^{131}$I-mAb A33 by the antigen-positive tumor tissue.

In the 17 patients treated with $^{131}$I-mAb A33, a total of 46 hepatic metastases were documented at surgery, and 45 of these were identified on whole body planar or spot view images of the abdomen. Two primary colon cancers were also visualized by external scans, while regional lymph node metastases, although having similar tumor:normal tissue ratios by biopsy-based dosimetry, could not be distinguished from adjacent sites of uptake in the abdomen.

Figure 2A:
FIG. 2 is an autoradiograph which shows that radioisotope $^{131}$I, when conjugated to mAb A33, is internalized into tumor cells and is not found in surrounding tissue.
Figure 2B:
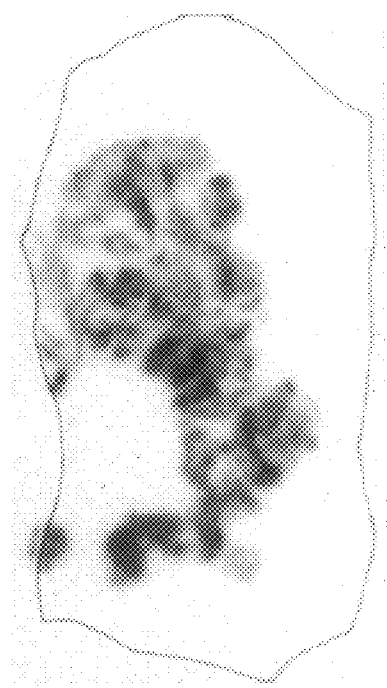

The vascularity of liver metastases was assessed with $^{99m}$Tc-HSA scans and biopsy-based dosimetry. The $^{99m}$Tc-HSA scans confirmed the hypovascularity characteristic of these lesions, which appeared as photopenic areas compared to the surrounding, uninvolved liver. Similarly, biopsies showed tumor:liver ratios for $^{99m}$Tc ranging from 0.14:1 to 1.19:1, with most lesions having values of less than 0.60. Tests with the negative control mAb, $^{131}$I-mAb TA99, showed minimal tumor uptake with faint positive imaging in only one patient, and tumor:liver ratios of 1.1:1 to 5.4:1. In contrast, $^{131}$-mAb A33 produced tumor:liver ratios up to 100:1 as determined from biopsies. Specific accumulation of $^{131}$I-mAb A33 in the hepatic lesions but not in surrounding normal liver was also visualized by combined autoradiography (see FIGS. 1 and 2) and immunohistochemistry with frozen tissue sections.

Variable localization of $^{131}$I-mAb A33 to the normal intestine was found. Scans in several patients showed labeling of some portions of the bowel, with clear outlines of the normal colon in some cases. However, in other cases, only minimal normal colon imaging was shown. Tests with sections of normal large bowel removed during surgery showed that a significant amount of radiolabel could be recovered by simply washing the specimens with phosphate-buffered saline. Thus, at least some of the apparent normal bowel uptake of $^{131}$I-mAb A33 may represent free $^{131}$I secreted by the stomach or monoclonal antibody if binding affinity was low. The finding that A33-positive normal small and large intestinal mucosa do not accumulate $^{131}$I-mAb A33 more consistently may be related to lack of accessibility of the antigen in the normal mucosa.

EXAMPLE IV

Therapeutic Effect of $^{131}$I-mAb A33 in Humans with Colon Cancer

A therapy trial of $^{131}$I-mAb A33 was conducted in patients with advanced colorectal cancer. Twenty-three patients were entered into the study and received 30 mCi/m$^2$ of $^{131}$I-mAb A33 as a single infusion or up to three infusions on consecutive days. Two patients (Nos. 14 and 18) were lost to follow-up (insufficient number of blood samples at nadir time) and two patients who died of progressive disease less than one month after treatment (Nos. 2 and 22) had incomplete evaluation of toxicity. Upon review of histologic slides, one patient (No. 10) was found to have small bowel cancer rather than colon cancer. For the patients included in this study, no frozen tissues for A33 immunohistochemistry were obtained, thus precluding antigen typing as a criterion for inclusion in the study. The available mAbs against A33 do not allow antigen detection in routinely fixed, paraffin-embedded material. One to 3 weeks after treatment, 20 of the 23 treated patients showed positive $^{131}$I-mAb A33 scans for tumor sites independently identified by computerized tomography (CT) or chest X-rays. Two patients with surgically documented intra-abdominal disease and rising CEA levels were not visualized by either CT or $^{131}$I-mAb A33 scan, and one patient (No. 10) with small bowel cancer had a negative $^{131}$I-mAb A33 scan.

All patients included in this study developed human anti-mouse antibody ("HAMA") responses after one treatment cycle, with titers of 1:10,000 to 1:100,000 for both IgM and IgG by 4 weeks post-treatment. The major toxicities observed were thrombocytopenia and neutropenia, and their severity was generally dose-dependent. However, for each dose level tested ($\geq 45$ mCi/m$^2$), patients with prior extensive chemotherapy showed the most pronounced and/or prolonged signs of bone marrow suppression, even if the platelet counts had returned to the normal range at the time of $^{131}$I-mAb A33 treatment. This patient variation in hematologic toxicity was not due to differences in $^{131}$I retention as measured by total body isotope clearance rates. Instead, it appeared to reflect an intrinsic sensitivity to radiation damage. Of the five patients treated with 75–84 mCi/m$^2$, one patient (No. 11) developed grade 3 thromocytopenia (nadir 33,000/µl for 2 days), and three patients (Nos. 13, 14 and 15) displayed no toxicity effects. Patients Nos. 11 and 12 had prior treatment with BCNU, streptozoticin, vincristine, 5-fluorouracil (5-FU), and leucovorin, whereas patients Nos. 13, 14 and 15 received only 5-FU and leucovorin.

Of the six fully evaluable patients who received 86–94 mCi/m$^2$ $^{131}$I-mAb A33 (Nos. 16, 17, 19, 20, 21 and 23), two (Nos. 21 and 23) showed grade 4 toxicity, one showed grade 1 toxicity, and three showed no toxicity. Of the two patients with grade 4 toxicity, patient No. 21, who had extensive prior chemotherapy (5-FU, interferon-α, BCNU, streptozotocin, and vincristine in separate protocols over a 30-month period), showed rapid and prolonged suppression of platelet and neutrophil counts after $^{131}$I-mAb A33 treatment. Neutropenia was seen in two patients (Nos. 21 and 23) with thrombocytopenia. Two additional patients (Nos. 18 and 22) who had only a single blood test during their nadir period, and were therefore not fully evaluable, had at least grade 2 and 3 neutrophil toxicity. Lymphocytopenia generally accompanied decreases in total white cell counts, but was not analyzed with regard to distinct lymphocyte subsets.

Treatment responses were evaluated in 18 patients who had disease which had been measured by either chest X-ray or CT scan, and three patients had disease measurable by serum CEA levels, but failed to show measurable disease by radiographic studies. Two patients were not evaluable due to loss to follow-up or surgical resection of the tumor. Evidence for mixed responses was obtained in five patients (Nos. 3, 5, 7, 9 and 23). Patient No. 3 presented liver metastases and cytology-proven, malignant ascites, which had been stabilized with diuretics (lasix, aldactone) before treatment. After $^{131}$I-mAb A33 infusion, extensive accumulation of radioisotope in the ascitic fluid was detected. One month after treatment, the patient's weight had decreased by 8 kg, the ascites had disappeared, and serum CEA levels had dropped from 3,750–4,200 ng/ml (before treatment) to 2,000 ng/ml. Subsequently, the diuretics were discontinued and serum CEA levels stabilized at 1,750 ng/ml for almost 4 months. The liver metastases remained unchanged by radiographic criteria. Retreatment with $^{131}$I-mAb A33 was attempted after 10 weeks; however, due to HAMA response, isotope accumulation was seen only in liver and spleen, and not in tumor sites.

Figure 3:
FIG. 3 represents the effect of $^{131}$I-mAb A33 on carcinomatous lesions.

Patient No. 5 had extensive pleural disease in the right chest, a measurable lesion in the left chest, and liver metastases. Three weeks after $^{131}$I-mAb A33 treatment, the left chest lesion appeared less well-defined, and 2 months later had disappeared (see FIG. 3). The other sites of measurable disease remained stable for 5 months. Patient No. 9 had extensive abdominal disease including liver metastases, a large pelvic mass, and large left supraclavicular and neck lymph nodes. Four weeks after $^{131}$I-mAb A33 treatment, the lymph nodes were no longer palpable, although a month later her pelvic mass showed an increase in size. In patients Nos. 7 and 23, serum CEA levels decreased by 22% and 30%, respectively, for more than 16 weeks; however, more detailed assessment of disease progression was not possible since neither patient had measurable disease by radiologic examination. A comparison of the patients with and without evidence of mixed responses has not revealed any consistent differences. In particular, no obvious correlation has emerged between the level of radioisotope uptake into tumor sites (determined from scans) and measurable responses.

Preparation of Antibody Conjugates

Monoclonal antibody A33 can be conjugated to anti-cancer drugs and administered to treat cancer. For example, mAb A33 can be conjugated with QFA, which is an antifolate, or with calicheamicin, which is an anti-tumor antibiotic that cleaves double-stranded DNA of tumor cells. Both QFA and calicheamicin have intracellular sites of action and do not readily cross the plasma membrane. Therefore, they have weak cytotoxic effects when added to cell cultures. Cellular uptake of these agents through mAb A33-mediated internalization greatly enhances their cytotoxic effects in vitro. In vivo xenograft studies show that tumor inhibition with limited normal tissue damage can be obtained with both mAb A33-QFA and mAb A33-calicheamicin conjugates. Other anti-cancer drugs can also be conjugated to the antibodies of the invention and used to treat cancer, including BCNU, streptozoicin, vincristine and 5-fluorouracil.

Monoclonal antibody A33 can also be used to target genetic material to both colon cancer cells and normal colonocytes since it is internalized rapidly into target cells. The A33 antigen directs the antibody to macropinosomes, which are compartments inside the cell. Transfected DNA also traverses the macropinosomal compartment, surviving hydrolysis and ultimately incorporating into chromosomal DNA. With mAb A33-drug conjugates, the A33 antibody directs reagents to the nuclear DNA. Similarly, genetic material can be directed inside the cell utilizing mAb A33.

EXAMPLE V

A33-Oligonucleotide Conjugate

A 26-mer oligonucleotide containing a free, reactive thiol group at the 3' end was conjugated to a free amine of mAb A33 using the heterobifunctional reagent SPDP. The 5' end of the oligonucleotide was enzymatically labelled with $^{32}P$ as tracer for DNA. SDS PAGE and reduced gels showed a pattern consistent with a product containing a range of oligonucleotide/mAb ratios. Purification was accomplished with protein A chromatography. The final product was sterile-filtered and tested for cell-binding activity and protein and bound oligonucleotide concentrations.

The final purified product was tested on an A33 antigen-expressing colon cancer cell line SW1222. Based on the ability of low pH to reverse mAb A33 binding to its antigen, a protocol was developed to quantify the percentage of internalization. This was used to analyze and compare binding and internalization of mAb A33-$^{32}P$-DNA with that of $^{125}I$-mAb A33. An excess of unlabelled and unmodified mAb A33 was used to block the specific binding of radiolabelled mAb A33 conjugates to cells. This demonstrated that all cell binding was specific and mediated through the interaction of mAb A33 and its antigen. The assay was done in 96-well plates with 100,000 cells per well in log phase growth. At 24 hours, 7.2% of $^{32}P$ added to the wells was bound to the cells. By 48 hours, over 60% of $^{32}P$ was internalized. Anti-tumor effects were observed in nude mice carrying transplanted SW1222 cells when anti-actin DNA was used. These conjugates also contained $^{32}P$ as a tracer, and it is possible that $^{32}P$ contributed somewhat to the anti-tumor effects. However, since the amount of radioactivity was low (10 µCi/mouse), minimal effects would be expected from the isotype alone.

The antibody conjugates of the invention can be administered via various routes known by those skilled in this field. By way of example, they can be administered intravenously, intraperitoneally, intramuscularly, subcutaneously or orally (e.g., attached to virus). The antibody conjugates of the invention can also be administered in combination with a pharmaceutically acceptable carrier in composition form. The antibody conjugates of the invention can be administered at a dose range of about 0.1 mg to 2000 mg. However, dose ranges will vary among patients to be treated, depending on the condition of the patient to be treated, the medical history of the patient, the means of administration and several other factors.

EXAMPLE VI

Characterization of the A33 System

In order to characterize the A33 system, several A33-positive colon cancer cell lines were used to determine the number of mAb A33 binding sites per cell. It was found that there are greater than 800,000 sites per cell. The avidity of mAb A33 binding was found to be high. The same cell lines were used to show that A33 is a rapidly internalizing antigen, with up to 90% internalization over a 24-hour period in humans. Studies of the binding kinetics of $^{125}I$-mAb A33 to cultured colon cancer cells, acid wash experiments, and SDS-gel analysis of cell extracts and culture supernatants showed that 80–85% of the internalized mAb A33 cycles through intracellular compartments and, within about 1–2 days, is released from the cells in intact, immunoreactive form. Only a small fraction of internalized $^{125}I$-mAb A33 appears to be degraded after internalization, and this degradation was partially blocked by inhibitors of lysosomal enzymes.

The mechanism of mAb A33 internalization involves macropinosomes. In vitro studies with mAb A33 conjugated with $^{125}I$, calicheamicin and QFA showed strong cytotoxic activity against A33-positive colon cancer cells but not against A33-negative tumor cell lines. Since all three conjugates act after intracellular uptake, it was determined that the internalizing capacity of A33 plays an essential role in the observed cytotoxic effects.

EXAMPLE VII

Generation of Other Murine Antibodies

The inventors have generated two additional mouse mAbs, designated mAb 100–210, which is of the IgG2b isotype, and mAb 100–310, which is of the IgG2a isotype. mAb 100–310 is described in U.S. patent application Ser. No. 08/273,277, the entirety of which is incorporated herein by reference. Hybridomas secreting monoclonal antibodies 100–210 and 100–310 were deposited under the Budapest Treaty on Nov. 30, 1994 and Apr. 28, 1992, respectively, with the American Type Culture Collection, Rockville, Md., and catalogued as ATCC Nos. HB 11764 and HB 11028, respectively. These monoclonal antibodies show the same patterns of reactivity as mAb A33. Monoclonal antibody 100–210 blocks mAb A33 binding in competitive radiobinding assays. This suggests that it binds to the same or a spatially related epitope on A33 antigen as mAb A33, whereas mAb 100–310 and mAb A33 do not cross-block each other, suggesting that they react with two distinct epitopes on the same cell surface protein on A33 antigen.

EXAMPLE VIII

Generation of Humanized A33 Antibodies

The use of high- or low-affinity mAbs or mAbs with faster or more delayed serum clearance for immunotherapy in cancer patients will vary for different antigenic targets, tumor types, intrinsic pharmacokinetic properties of the mAbs, intended effector mechanisms, and other nonimmunologic parameters. Since mAb A33 shows excellent targeting properties in vivo, it provides an effective test system for evaluating these parameters. Humanized and modified monoclonal antibodies have been produced from mAb A33.

In order to clone and express the genes for mAb for A33, mAb A33 hybridoma cells were cultured in RPMI 1640 medium supplemented with 10% fetal calf serum and 1 mM glutamine. Total RNA was prepared from $10^9$ hybridoma cells using guanadinium isothiocyanate and poly(A+) mRNA isolated by oligo (dT) affinity chromatography. First strand cDNA was synthesized from 10 mg mRNA. DNA sequences encoding A33 variable domains, including signal sequences for secretion, were amplified from the cDNA using the pCR procedure described by Jones et al., *Bio/Technology*, 9:88–89 (1991), but with primers designed to allow facile cloning of the PCR products into vectors for expression in mammalian cells. These vectors were derived initially from pEE6 (Stevens et al., *Nucl. Acids Res.*, 17:7110 (1989).

Figure 4A:
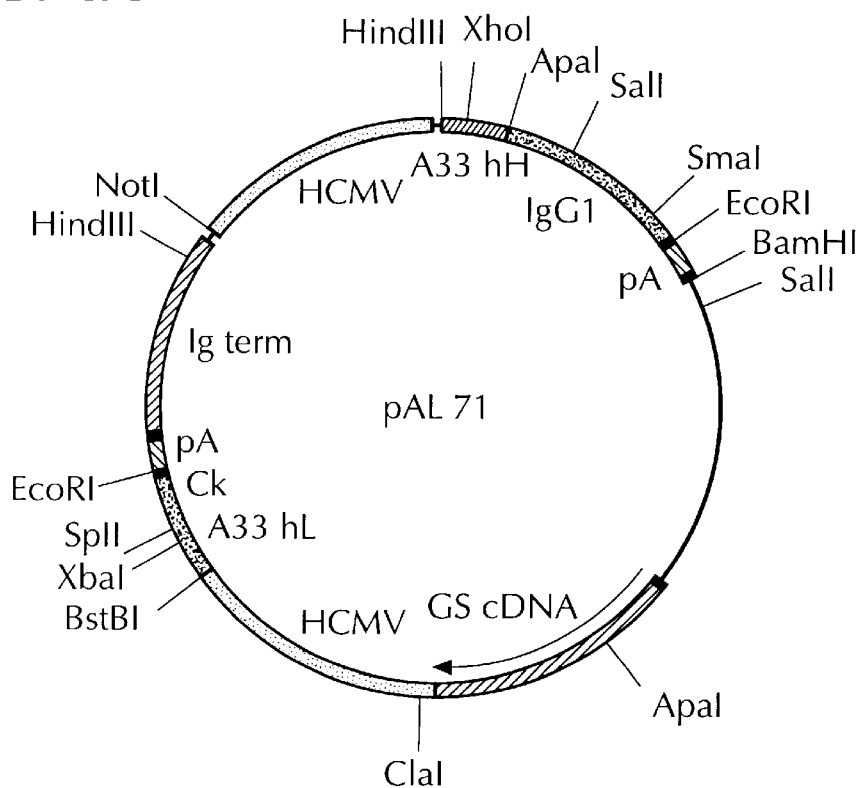
FIGS. 4A and 4B represent vectors which encode hA33 IgG1 and hA33 Fab'Δcys, respectively.
Figure 4B:
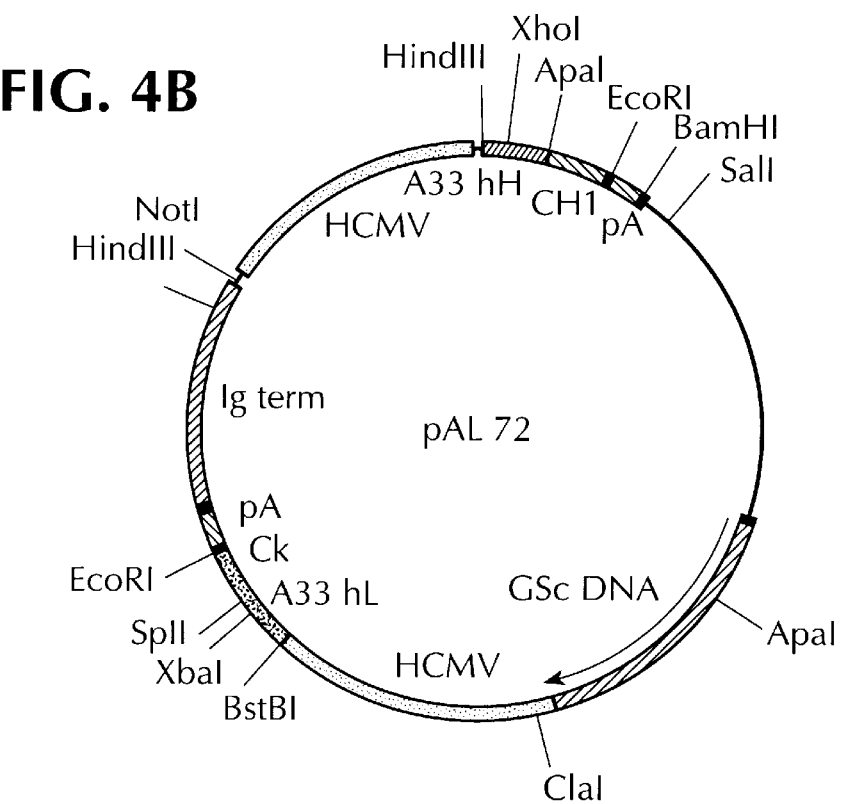

FIG. 4 shows final NSO expression vectors. PCR amplified fragments for the light chain variable domain were cloned between the Bst1 and Spl1 sites of pMRR010, a pEE6 derivative constructed to allow expression of such sequences as kappa chimeric light chains. PCR amplified fragments for the A33 heavy chain variable domain were cloned between the HindIII and ApaI sites of pMRR011, a pEE6 derivative constructed to allow expression of such sequences as gamma 1 chimeric heavy chains. The cloned variable region genes were sequenced by the double strand dideoxy chain terminating method using T7 DNA polymerase.

The humanized variable domains were assembled by the procedure disclosed by Daugherty et al., *Nucl. Acids Res.,* 19:2471–2476 (1991) using primers which allowed facile cloning into pMRR010 and pMRR011 for the light and heavy chains, respectively. These humanized variable region genes were sequenced by the same procedures used for the murine variable region genes. An expression vector for the hA33 Fab'Δcys heavy chain with a single hinge thiol was constructed by replacing the gamma 1 constant domains with the appropriate segment from the cB72.3 Fab'Δcys gene described by King et al, *Cancer Res.,* 54:6176–6185 (1994).

Transient co-expression of murine IgG heavy and light chains, or humanized IgG and Fab' heavy and light chains was achieved by co-transfection of the separate expression vectors into CHO-L761 hour cells as described by Cockett et al., *Bio/Technology,* 8:662–667 (1990). For stable cell line development the heavy and light chain expression, units were combined in a single plasmid. This was accomplished by replacing the Not1-BamH1 stuffer fragment in the light chain expression plasmids with the Not1-BamH1 fragments carrying the hCMV promoter/enhancer and heavy chain genes from the heavy chain expression plasmids. The final expression plasmids were termed pAL71 and pAL72 for hA33 IgG1 and Fab'Δcys, respectively (FIG. 4).

Stable NSO cell lines for the production of hIgG1 and hFab' were then established by transfecting the plasmids according to the procedure taught by Bebbington et al., *Bio/Technology,* 10:169–175 (1992). After transfection, the cells were plated at $2 \times 10^5$ cells per 96-well plate in Dulbecco's Modified Eagles Medium containing 10% dialysed fetal calf serum and 2 mM glutamine. After 24 hours cells were selected by the addition of methionine sulphoximine to the medium at a final concentration of 7 μM. After 21 days of culture, resistant colonies were picked and expanded for analysis of productivity. The highest producers were selected for production of recombinant antibody in roller bottle culture.

The results of these binding assays showed that chimeric antibody bound to cells expressing the antigen as well as murine A33, confirming that the cloned genes correspond to those of A33. FIG. 5 shows the amino acid sequences of the heavy and light chains deduced from the DNA sequence of the cloned variable domain genes. N-terminal protein sequencing of the first 11 amino acids gave results completely consistent with these deduced amino acid sequences for both heavy and light chains, confirming that the appropriate genes had been cloned.

FIG. 5 shows the amino acid sequences of the light [A] and heavy [B] chain variable domains of the murine and humanized A33 antibodies. The sequence of the mouse antibody as deduced from cDNA (mA33) SEQ ID NO:1, light chain, and SEQ ID NO:3, heavy chain is shown aligned with the humanized antibody sequence (hA33) SEQ ID NO:2, light chain, and SEQ ID NO:4, heavy chain. The humanized framework sequence is derived from the human antibody LAY (Kabat et al., *Sequences of Proteins of Immunological Interest,* 4th Ed. (1987)). The three complementarity determining regions in each chain are underlined. Residues in the LAY framework that have been replaced with mouse A33 sequence are double underlined.

The $V_H$ of A33 shows closest homology (70%) to the consensus sequence of human subgroup $V_H$III, while the $V_L$ shows greatest homology to the consensus sequence of human subgroups $V_L$I and $V_L$I (62%). It was from these subgroups that LAY, which has a $V_H$III heavy chain and $V_L$I light chain, was chosen as the human framework. In FIG. 5, the light chain residues 1–23, 35–45, 47–49, 57–86, 88 and 98–108 inclusive were derived from the LAY sequence, and the residues 24–34, 46, 50–56, 87 and 89–97 correspond to the Complementarity Determining Regions (CDRs). Residues 46 and 87 are predicted to be at the interface of the light and heavy variable regions. Residue 46 is usually a leucine in human antibody sequences, and residue 87 is usually a phenylalanine or tyrosine.

For the heavy chain, residues 2–26, 36–49, 66–71, 74–82a, 82c-85, 87–93 and 103 to 113 inclusive were derived from the LAY sequence while residues 1, 27–35, 50–65, 72, 73, 82b, 86 and 94–102 inclusive were derived from the murine sequence. Residues 31–35, 50–65 and 95–102 in the heavy chain correspond to the CDRs. The murine derived amino acids in the framework regions were included for several reasons: residue 1 is usually solvent accessible and in the vicinity of the CDR region (residues 27–20); LAY has a residue, alanine, not normally found at this position in human or murine $V_H$ sequences and therefore the murine residue was used. Also, at positions 72 and 73, the murine residue was used because of the predicted proximity to CDR2 and, in the case of residue 72, to remove the possibility of introducing an N-linked glycosylation site into the variable domain by the use of the LAY framework. The murine sequence was also used at the inter-domain residue 94, where A33 has a proline, not normally found at this position. Murine residues were used at positions 82 and 86 because the use of the human amino acids at these positions in a humanized antibody with LAY frameworks has previously been found to be deleterious for the expression of the heavy chain.

hIgG was purified from tissue culture supernatants of NSO cells using protein A-Sepharose affinity chromatography and characterized by SDS-PAGE as described by King et al., *Biochem.,* 281:317–323 (1992). hA33 Fab'Δcys was purified from cell culture supernatant by chromatography on protein A-Sepharose using the low affinity protein A binding site on Fab' as a basis for purification. A column of protein A-Sepharose was equilibrated with 100 mM boric acid buffer pH 8.0 containing 150 mM sodium chloride. The tissue culture supernatant from NSO cells expressing hA33 Fab'Δcys was adjusted to pH 8.0 by the addition of 1M tris and applied to the column. After washing with the equilibration buffer, the Fab' was eluted with 0.1M citric acid, collecting fractions directly into sufficient 1M tris to immediately adjust the pH of the fraction to between 6 and 7.

After dialysis and ultrafiltration, hA33 Fab'Δcys was cross-linked to DFM™ and TFM™ using the maleimide-based homobifunctional and homotrifunctional linkers CT52 and CT998 respectively, as described for cB72.3 Fab'Δcys by King et al., (1994) supra. These cross-linkers contain the 12N4 macrocycle for incorporation of $^{90}$Y. The DFM™ and TFM™ produced were purified by gel filtration using a Sephacryl S-200HR column. Radiolabelling with $^{90}$Y was performed as described by King et al., (1994) supra.

Small amounts of the humanized antibody were produced in a transient expression system in CHO cells to establish that it bound SW1222 cells expressing the antigen. Stable NSO cell lines were then isolated to produce larger quantities of purified material, for both hA33 IgG and Fab'Δcys. The best lines produced approximately 700 mg/ml of hA33 IgG1 and 500 mg/ml of Fab'Δcys in suspension culture.

Figure 6A:
FIGS. 6A and 6B represent SDS polyacrylamide gels of humanized IgG and TFM(Tri-Fab') under reducing (FIG. 6A) and non-reducing (FIG. 6B) conditions.
Figure 6B:
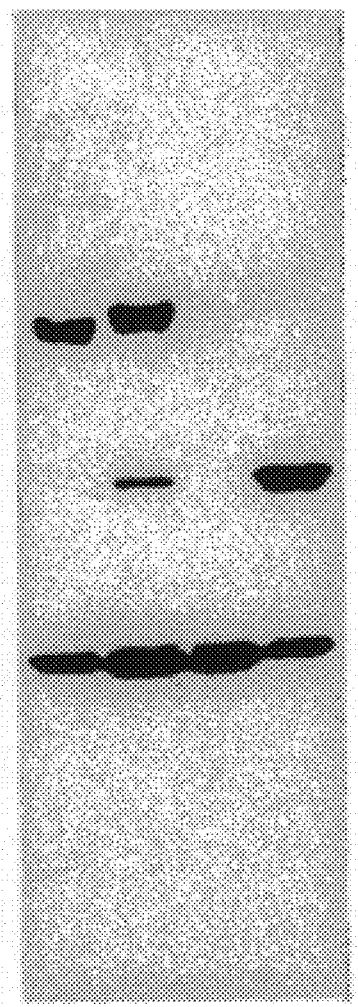

FIG. 6 shows SDS polyacrylamide gel of humanized A33 IgG and TFM™ under (A) non-reducing and (B) reducing conditions. Lane 1, hA33 IgG; lane 2, hA33 Fab'Δcys; lane 3 hA33 Fab'Δcys cross-linking mix; lane 4 purified hA33 TFM™.

FIG. 6 demonstrates that the purified hIgG was homogeneous and fully assembled. HPLC analysis demonstrated that it was free of aggregates. As expected, the hFab'Δcys was recovered largely in the form of monovalent Fab' with little in the form of F(ab')$_2$, consistent with results for other recombinant Fab' fragments. SDS-PAGE analysis of the purified TFM™ showed a single species of approximately 150 kD under non-reducing conditions. Under reducing conditions, two species of approximately 75 kD and 25 kD were observed, corresponding to the sizes expected for three cross-linked Fd' chains and light chains, respectively.

Figure 7A:
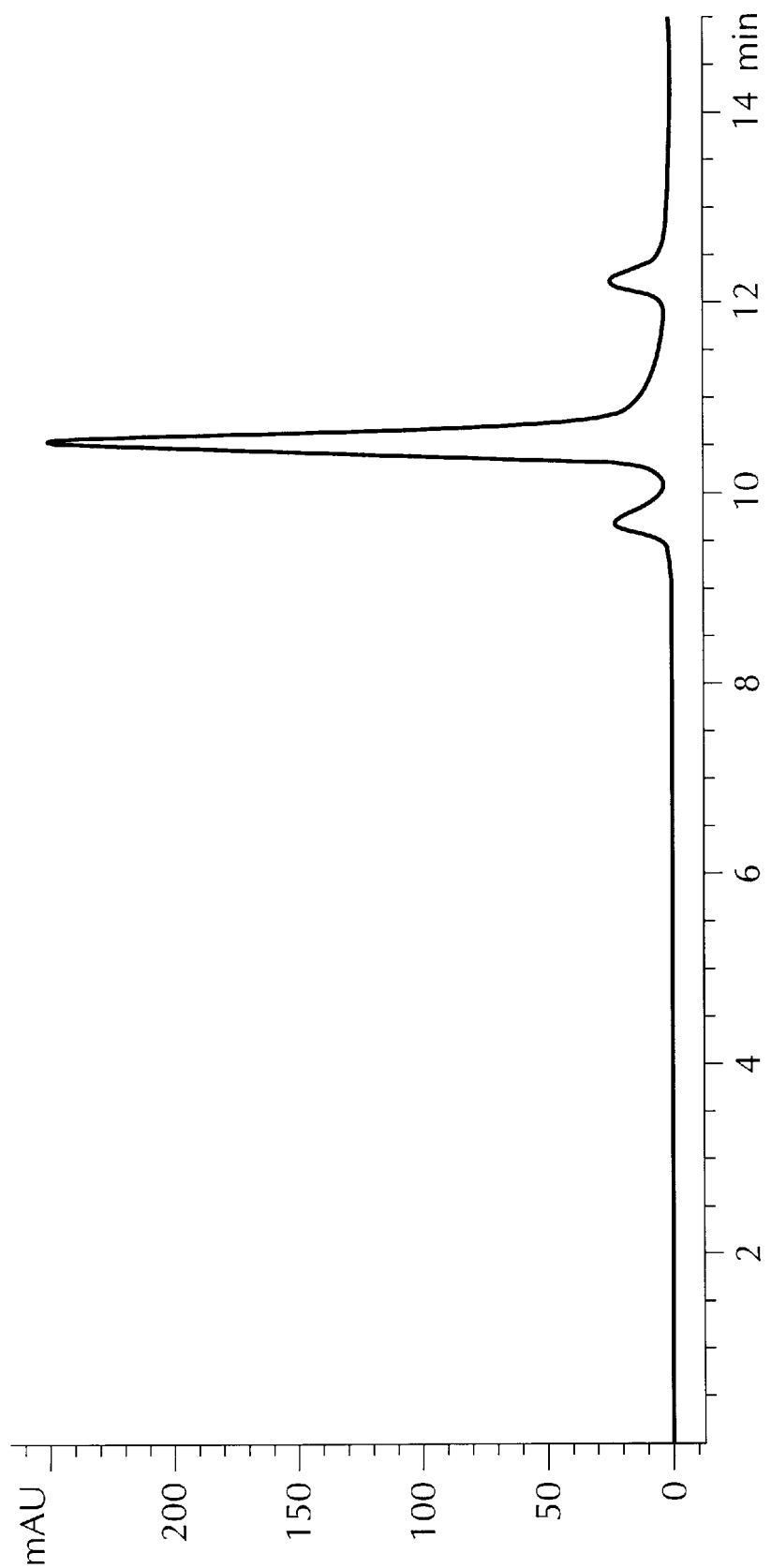
FIGS. 7A, 7B and 7C represent HPLC profiles of hA33 Fab' (FIG. 7A), hA3Fab' after cross linking to trivalent Fab fragments (hereafter "TFM™") (FIG. 7B), and purified hA33 TFM™ (FIG. 7C).
Figure 7B:
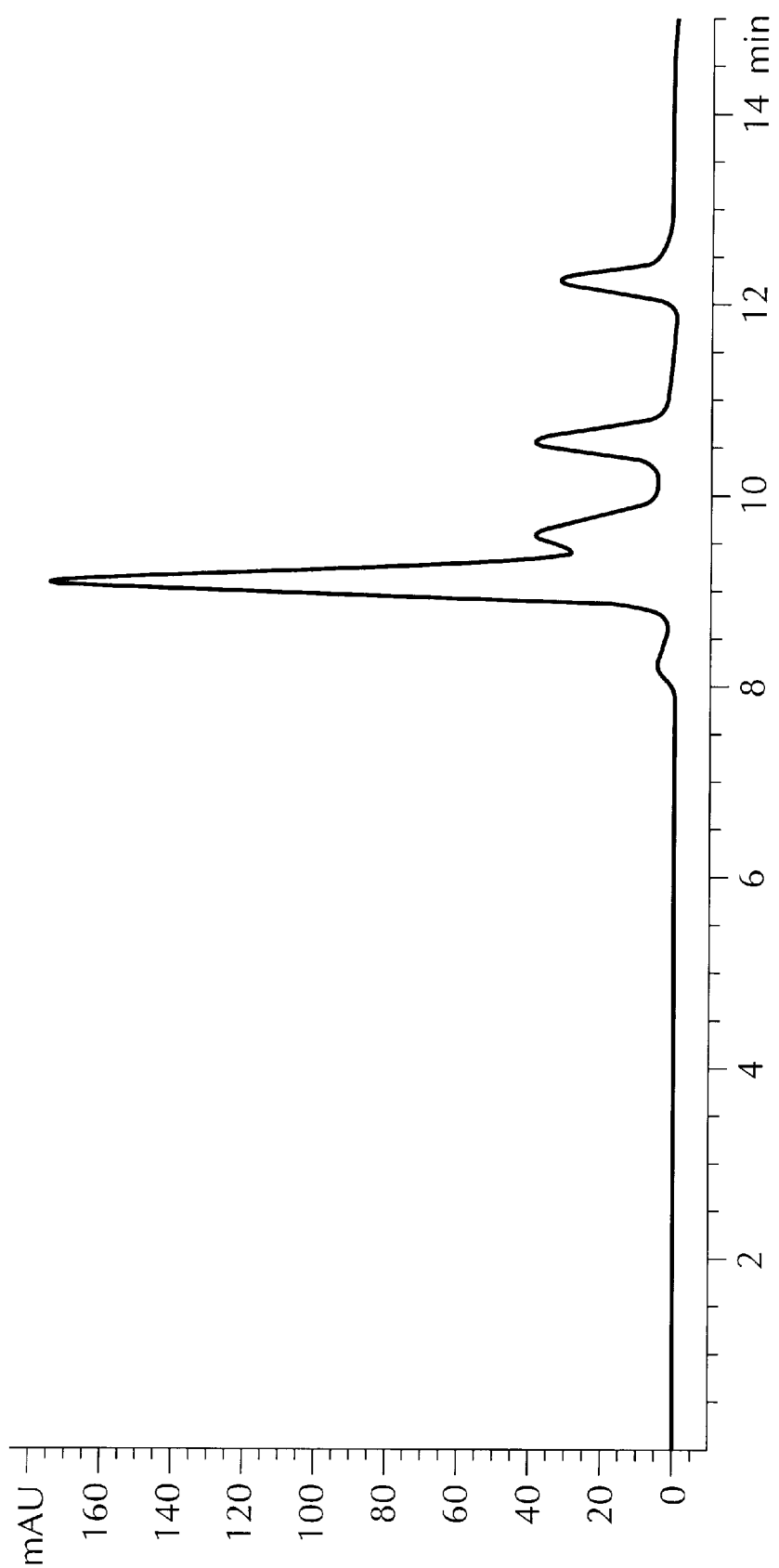
Figure 7C:
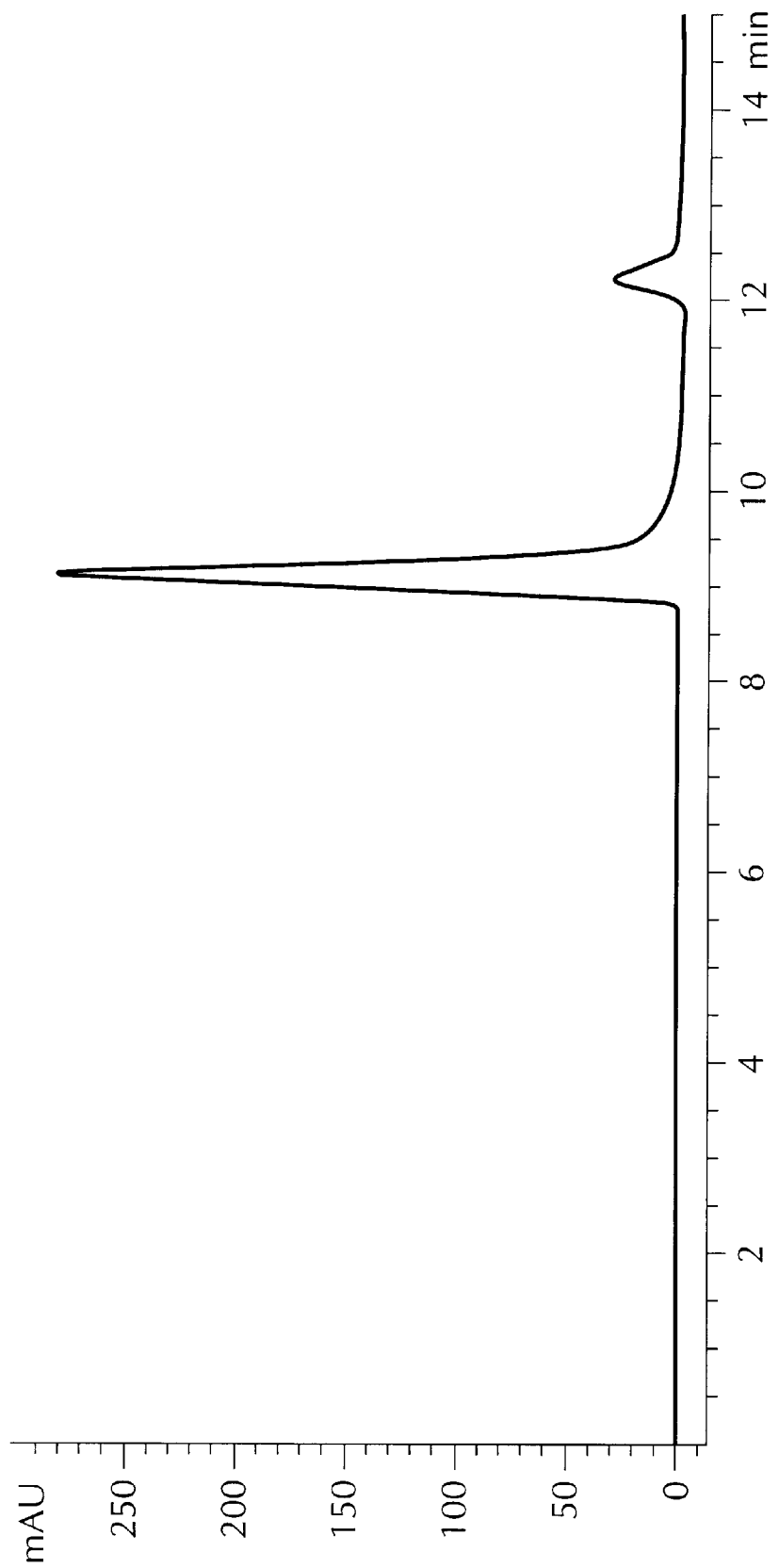

Cross-linking of Fab'Δcys to TFM™ was achieved with a yield of 60–65%. FIG. 7 shows HPLC profiles at 280 nm of (a) hA33 Fab'; (b) hA33 Fab' after cross-linking to TFM™ and (c) purified hA33 TFM™. HPLC gel filtration was carried out on a DuPont Zorbax GF-250 column run at 1 ml/min in 0.2M sodium phosphate buffer pH 7.0. As shown in (a) hA33 Fab' peak has a retention time of 10.5 minutes with a minor peak of F(ab')$_2$ at 9.7 minutes and a buffer peak at 12.2 minutes. As shown in (b) after cross-linking, the major peak represents TFM™ at 9.0 minutes. Minor peaks represent di-Fab at 9.6 minutes, residual monomeric Fab' at 10.5 minutes, a small amount of aggregate at 8.2 minutes and the same buffer peak at 12.2 minutes. As shown in (c), after purification, the TFM™ peak is still seen at 9.0 minutes, the only other visible peak being the buffer peak at 12.2 minutes.

Antigen binding assays were then performed using cells of two human colorectal tumor cell liens which express the A33 antigen, COLO 205 and SW1222. These cells were cultured in DMEM medium containing 2 mM glutamine and 10% fetal calf serum. Assembled antibody in culture supernatants and in purified preparations was quantitated in an ELISA. Direct binding of murine an humanized antibodies in SW1222 cells was measured in a FACScan assay. SW1222 cells were trypsinized to remove them from culture flasks, washed with phosphate buffered saline (PBS) and resuspended in PBS containing 10% bovine serum and 0.1% sodium azide. Humanized A33 antibody was serially diluted in PBS containing 10% FCS and 0.1% sodium azide and added to 2×10$^5$ cells. Following a one hour incubation on ice, the cells were washed in PBS and then incubated with a rhodamine anti-(human Fc) conjugate (1:1000 in PBS, 10% FCS and 0.1% sodium azide) for one further hour on ice. After washing in PBS, the amount of rhodamine labelled A33 antibody conjugate bound to the cells was measured in a FACScan analyzer. Direct binding of murine A33 was measured by FACScan analysis after incubation of SW1222 cells with FITC-labelled antibody. Suitable non-specific antibody controls were carried out to demonstrate that A33 binds specifically via antibody-antigen interaction rather than non-specifically through Fc interactions.

Determination of affinities of murine and humanized antibodies was based on the procedure described by Krause et al., *Behring Inst. Mitt.*, 87:56–67 (1990). Briefly, antibodies were labelled with fluorescein using fluorescein isothiocyanate (FITC) titrated from 1.3 mg/ml, and then incubated with 2.8×10$^5$ SW1222 cells for two hours on ice in 350 ml PBS containing 5% FCS and 0.1% sodium azide. The amount of fluorescence bound per cell was determined in a FACScan and calibrated using standard beads. The number of molecules of antibody that had bound per cell at each antibody concentration was thus established and used to generate Scatchard plots. Competition assays were performed by FACScan quantitation of bound FITC-labelled murine A33 after incubating SW1222 cells with a standard quantity of the murine antibody together with a dilution series of the humanized variants.

Figure 8:
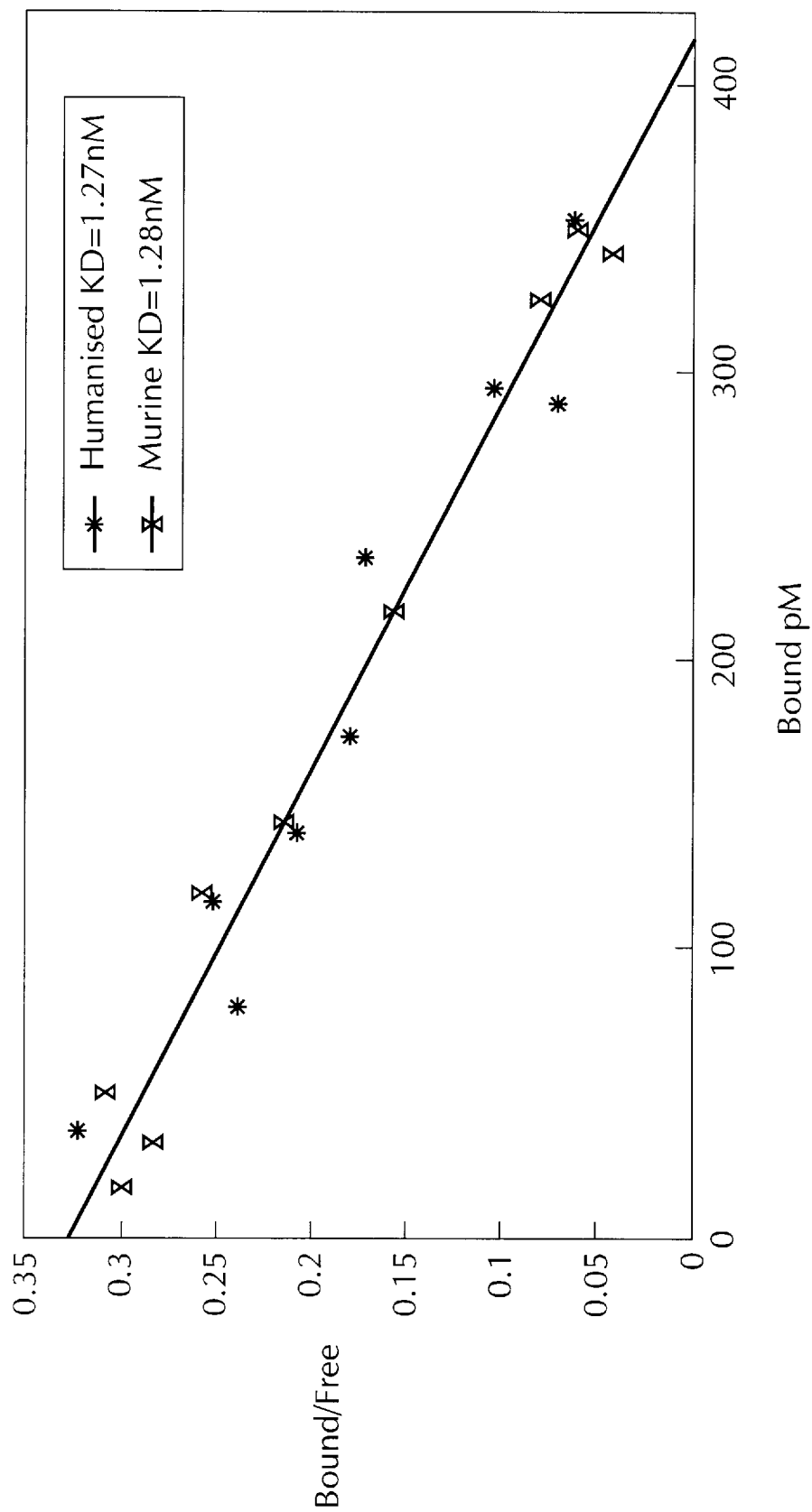
FIG. 8 represents a Scatchard plot of humanized and mouse A33 binding to SW1222 cells.

FIG. 8 shows Scatchard analysis for the murine antibody and hIgG1 binding to SW1222 cells. These data suggest that both antibody forms have equilibrium dissociation constants ($K^D$'s) of 1.3 nM and have approximately 300,000 sites per cell. The antigen binding activity of hTFM™ was compared to those of monovalent hFab'Δcys and hIgG in competition binding assays in which these species were competed with murine IgG for binding to COLO 205 cells expressing the antigen. The results (FIG. 9) demonstrate that the monovalent Fab' fragment binds less well than the bivalent IgG, as expected. The trivalent hTFM™, on the other hand, showed approximately twofold better binding than hIgG, presumably as a result of increased avidity. This finding is consistent with results for chimeric B72.3, for which TFM™ also showed two to threefold better binding than IgG.

Figure 9:
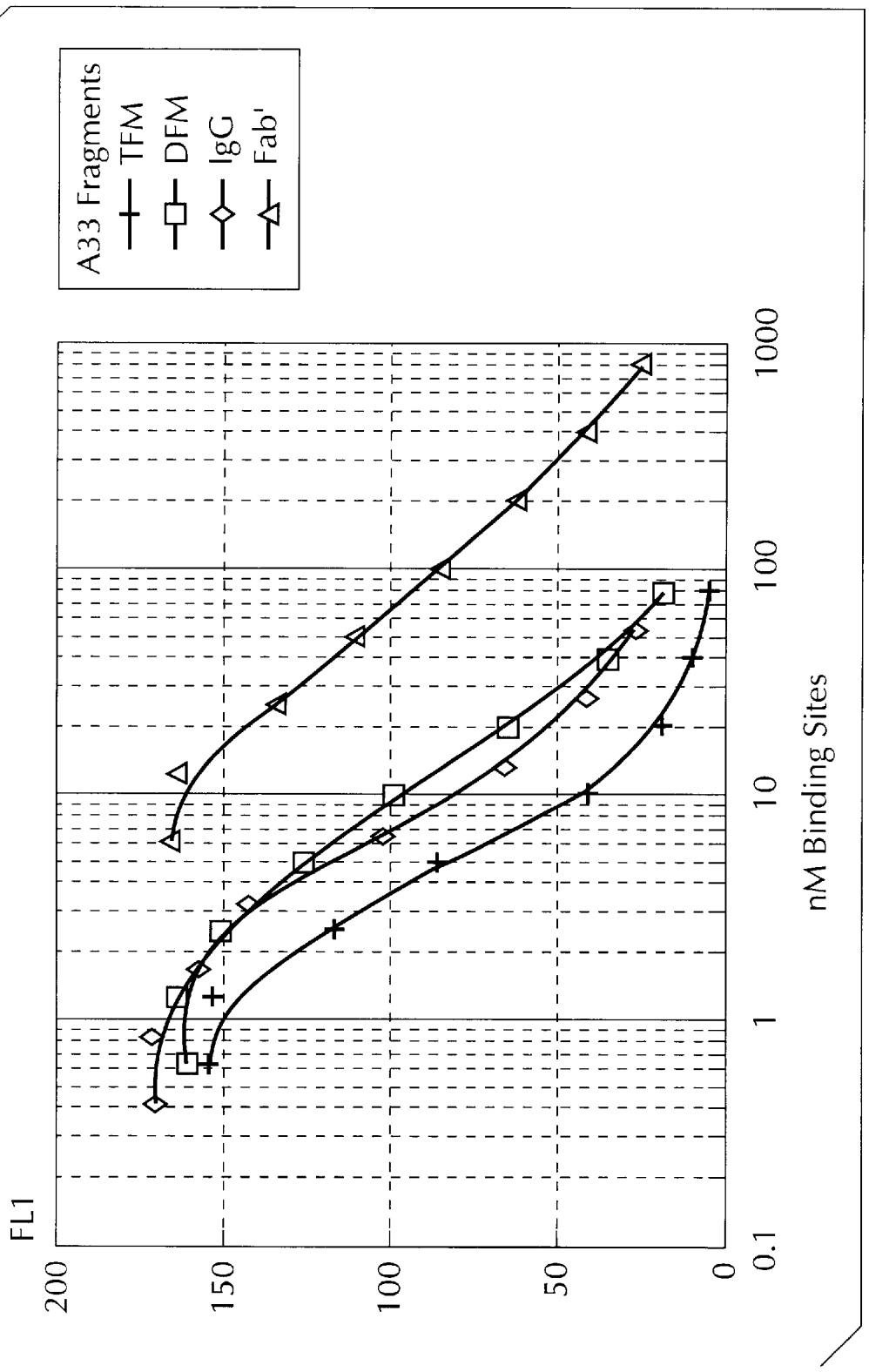
FIG. 9 represents a competitive binding assay for hA33 Fab'Δcys, IgG and TFM™ binding to COLO 205 cells.

FIG. 8 shows a Scatchard plot of humanized and murine A33 binding to SW1222 cells. Experimental details as in materials and methods. Kd values of 1.28 nM for murine A33 IgG and 1.27 nM for humanized A33 IgG were calculated from linear regression analysis of the data points. FIG. 9 represents the competitive binding assay for hA33 Fab'Δcys, IgG and TFM™ binding to COLO 205 cells. hA33 IgG (◇), TFM™ ▮ DFM™ (□), and Fab'Δcys (Δ) were competed with FITC labelled murine A33 IgG and results plotted as fluorescence units versus nM binding sites.

Antibodies were then labelled with $^{90}$Y via the macrocyclic ligand tetraazocyclododecane etra-acid, (termed 12N4 or DOTA) coupled to the immunoglobulin via 12N4-maleimide linkers as described by Antoniw et al., "Practical evaluation of yttrium-90 labelled monoclonal antibody A33 and A33 tri-fab (TFM) for radioimmunotherapy of colorectal carcinoma", *In Press*. Radiolabelling of hA33-12N4 conjugates with $^{90}$Y and $^{125}$I, and biodistribution studies in nude mice bearing subcutaneous SW1222 tumor xenografts, were carried out as described by Antoniw et al., supra. Antibodies were labelled with $^{111}$In via a second macrocyclic ligand, 1,4,7-triazacyclononanetriacetic acid or 9N3 using 9N3-maleimide linkers as described by Turner et al., *Br. J. Cancer*, 70:35–41 (1994). The immunoconjugate was shown to be fully immunoreactive using the competition based FACs assay both before and after radiolabelling. For biodistribution experiments, radiolabelling was achieved to a specific activity of 2 μCi/μg with >95% incorporation of $^{90}$Y.

Biodistribution studies in guinea pigs were carried out after i.v. administration to male outbred Dunkin-Hartley guinea pigs of approximately 250–300 grams. Groups of four guinea pigs were injected with each $^{90}$Y-labelled component into the ear vein and sacrificed post administration at the time intervals indicated in FIG. 10. Blood samples were taken and tissues processed as described for mice by Antoniw et al., supra. Pharmacokinetic studies in cynomolgous monkeys of 5–7 kg (2 per group) were also carried out after i.v. injection of radiolabelled components. Blood samples were taken at 0.5, 1, 2, 4, 6, 8, 24, 48, 72, 96, 120, 144 and 168 hours for counting.

Figure 10:
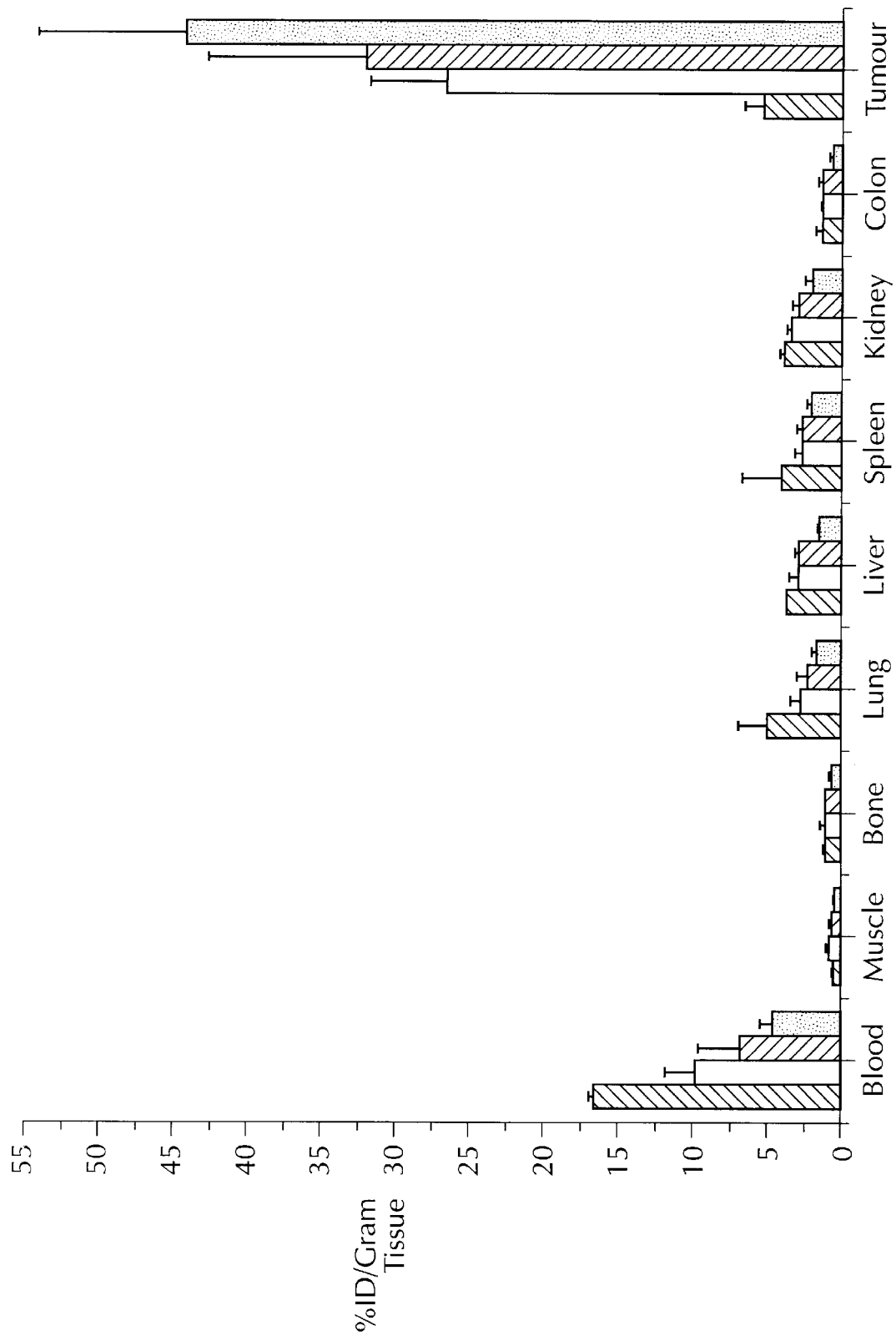
FIG. 10 shows biodistribution of $^{90}$Y-labelled humanized A33 in nude mice bearing SW1222 tumor xenografts.

FIG. 10 shows the time course study for biodistribution of $^{90}$Y-labelled humanized A33 in nude mice bearing SW1222 tumor xenografts. Mice were injected i.v. with 19 μCi (10 μg) $^{90}$Y-labelled hA33 each. Groups of 4 mice were killed at ▨ 24 (□), 48 ▧ and 144 hours ▨ post administration, and the amount of activity was determined in tumor and normal tissues. Each column represents the mean obtained from 4 mice. Error bars represent the standard deviation of the mean. Tissue uptake is plotted as % injected dose per gram of tissue. A favorable biodistribution was achieved, with high levels of activity localized to the tumor and little or no accumulation in any normal tissue. The biodistribution of the humanized A33 immunoconjugate was not significantly different from that of the murine antibody in the same xenograft system at these time points. For both the murine and humanized antibodies the level of activity localized to the tumor increased with time, even though levels in all other tissues were falling, which led to increasing tumor to normal tissue ratios over time (Table 2).

To assess whether this was a feature of the antibody itself or the radioisotope used, a biodistribution experiment was also carried out with humanized A33 labelled with $^{125}$I. In this experiment, the absolute levels of isotope retained by the tumor were slightly lower but the tumor to blood ratios were very similar, suggesting that the increasing localization is a property of the A33 antibody rather than the nature of the isotope/chelator system. The lower absolute levels of $^{125}$I-hA33 localized to the tumor are probably the result of dehalogenation of the radioiodinated antibody.

TABLE 2

(a) $^{90}$Y Humanized A33
Time Post Injection

|  | 3 h | 24 h | 48 h | 144 h |
|---|---|---|---|---|
| BLOOD | 0.32 ± 0.08 | 2.77 ± 0.38 | 5.63 ± 1.84 | 10.1 ± 2.60 |
| MUSCLE | 12.8 ± 4.95 | 34.3 ± 5.93 | 48.6 ± 8.35 | 127.3 ± 38.0 |
| BONE | 5.31 ± 2.27 | 24.4 ± 2.14 | 32.4 ± 11.2 | 68.5 ± 21.4 |
| LUNG | 1.29 ± 0.56 | 9.81 ± 2.03 | 13.7 ± 1.02 | 26.5 ± 8.39 |
| LIVER | 1.50 ± 0.37 | 9.50 ± 1.28 | 11.8 ± 4.54 | 30.7 ± 9.02 |
| SPLEEN | 1.77 ± 0.92 | 10.1 ± 1.42 | 12.8 ± 4.91 | 20.7 ± 5.47 |
| KIDNEY | 1.33 ± 0.25 | 7.75 ± 1.25 | 10.3 ± 2.17 | 21.3 ± 5.60 |
| COLON | 3.90 ± 1.04 | 19.2 ± 2.78 | 25.7 ± 10.5 | 56.7 ± 14.5 |

(b) $^{125}$I Humanized A33
Time Post Injection

|  | 3 h | 24 h | 48 h | 168 h |
|---|---|---|---|---|
| BLOOD | 0.36 ± 0.05 | 2.44 ± 0.09 | 4.75 ± 0.83 | 8.92 ± 2.12 |
| MUSCLE | 10.8 ± 3.47 | 27.3 ± 10.2 | 42.7 ± 9.67 | 75.5 ± 19.9 |
| BONE | 4.86 ± 1.20 | 28.9 ± 8.88 | 41.5 ± 9.74 | 74.5 ± 21.5 |
| LUNG | 1.39 ± 0.26 | 8.16 ± 0.59 | 14.2 ± 2.24 | 25.1 ± 6.78 |
| LIVER | 1.12 ± 0.08 | 8.01 ± 1.80 | 17.8 ± 3.61 | 32.8 ± 9.13 |
| SPLEEN | 1.67 ± 0.31 | 17.3 ± 2.54 | 29.9 ± 6.12 | 45.7 ± 18.5 |
| KIDNEY | 1.23 ± 0.21 | 9.92 ± 0.78 | 18.2 ± 3.40 | 33.2 ± 9.88 |
| COLON | 5.30 ± 1.38 | 22.8 ± 4.00 | 33.5 ± 6.34 | 60.5 ± 15.9 |

It was consistently observed that humanized TFM™ and all other humanized fragments examined clear aberrantly quickly from the circulation of mice, far more quickly than the equivalent murine fragments. This phenomenon was shown to be specific to mice and did not occur in rats, guinea pigs or monkeys. Table 3 shows a comparison of biodistribution for hA33 IgG, DFM™ and TFM™ in guinea pigs. It demonstrates the more rapid blood clearance of the DFM™ and TFM™, with blood activities falling to 0.01 and 0.02% i.d./g respectively at the 144 hours time point. Blood activity for hIgG was much higher, at 0.4% i.d./g, at this time point. Table 3 demonstrates very clearly that for DFM™, much higher levels of radioactivity are taken up by the kidney than for IgG and TFM™. This high activity for the DFM™ clears much more slowly from the kidney than from the blood. At early time points, kidney levels were a little higher for TFM™ and IgG, but much lower than for DFM™, and the activity cleared much faster from the kidney for TFM™ than for DFM™. These results for A33 are consistent with those for DFM and TFM™ of cB72.3, and are consistent with the view that the kidney is the organ of clearance for TFM™.

TABLE 3

Time Post Injection

|  | 24 h | 48 h | 72 h | 144 h |
|---|---|---|---|---|
| (a) $^{90}$Y Humanized A33 | | | | |
| BLOOD | 0.88 ± 0.04 | 0.75 ± 0.06 | 0.47 ± 0.12 | 0.40 ±0.09 |
| MUSCLE | 0.07 ± 0.01 | 0.07 ± 0.005 | 0.04 ± 0.01 | 0.04 ± 0.01 |
| BONE | 0.15 ± 0.01 | 0.13 ± 0.02 | 0.08 ± 0.02 | 0.07 ± 0.02 |
| LUNG | 0.29 ± 0.02 | 0.25 ± 0.02 | 0.16 ± 0.05 | 0.17 ± 0.05 |
| LIVER | 0.27 ± 0.08 | 0.24 ± 0.02 | 0.17 ± 0.04 | 0.16 ± 0.04 |
| SPLEEN | 0.30 ± 0.06 | 0.31 ± 0.03 | 0.26 ± 0.06 | 0.20 ± 0.02 |
| KIDNEY | 0.27 ± 0.003 | 0.27 ± 0.02 | 0.18 ± 0.05 | 0.20 ± 0.05 |
| COLON | 0.12 ± 0.01 | 0.12 ± 0.01 | 0.08 ± 0.02 | 0.07 ± 0.14 |
| (b) $^{90}$Y hA33 TFM ™ | | | | |
| BLOOD | 0.58 ± 0.10 | 0.22 ± 0.05 | 0.12 ± 0.01 | 0.02 ± 0.005 |
| MUSCLE | 0.03 ± 0.01 | 0.02 ± 0.007 | 0.01 ± 0.001 | 0.01 ± 0.001 |
| BONE | 0.16 ± 0.03 | 0.06 ± 0.02 | 0.04 ± 0.01 | 0.01 ± 0.002 |
| LUNG | 0.28 ± 0.04 | 0.12 ± 0.03 | 0.08 ± 0.01 | 0.02 ± 0.003 |
| LIVER | 0.28 ± 0.05 | 0.14 ± 0.05 | 0.09 ± 0.01 | 0.04 ± 0.006 |
| SPLEEN | 0.22 ± 0.03 | 0.11 ± 0.04 | 0.07 ± 0.01 | 0.04 ± 0.003 |
| KIDNEY | 1.08 ± 0.25 | 0.58 ± 0.22 | 0.49 ± 0.04 | 0.23 ± 0.03 |
| COLON | 0.13 ± 0.03 | 0.5 ± 0.01 | 0.04 ± 0.004 | 0.02 ± 0.001 |
| (c) $^{90}$Y hA33 DFM ™ | | | | |
| BLOOD | 0.17 ± 0.10 | 0.08 ± 0.01 | 0.04 ± 0.05 | 0.01 ± 0.002 |
| MUSCLE | 0.03 ± 0.002 | 0.02 ± 0.002 | 0.02 ± 0.03 | 0.01 ± 0.002 |
| BONE | 0.10 ± 0.01 | 0.08 ± 0.01 | 0.07 ± 0.01 | 0.06 ± 0.012 |
| LUNG | 0.14 ± 0.01 | 0.09 ± 0.01 | 0.06 ± 0.01 | 0.04 ± 0.01 |
| LIVER | 0.28 ± 0.03 | 0.22 ± 0.03 | 0.18 ± 0.03 | 0.12 ± 0.02 |
| SPLEEN | 0.26 ± 0.01 | 0.26 ± 0.06 | 0.21 ± 0.06 | 0.16 ± 0.04 |
| KIDNEY | 9.31 ± 1.56 | 8.60 ± 0.98 | 5.97 ± 1.41 | 4.27 ± 0.37 |
| COLON | 0.11 ± 0.02 | 0.07 ± 0.01 | 0.07 ± 0.01 | 0.05 ± 0.01 |

An exponential, nonlinear least-squares fitting procedure was used to determine the blood clearance parameters for each monkey. Mean values of the blood clearance parameters for IgG, TFM™ and DFM™ were used to set up appropriate integrals to calculate the percent of absorbed dose as a function of time post administration. Estimates were made as to the absorbed dose for red marrow which would be delivered by each form of the antibody (IgG, TFM™ and DFM™) in humans when labelled with $^{90}$Y. The monkey data showed that at early times, all of the administered activity was in the blood circulation, and this was taken to be the case for humans. Calculations were made based on the assumptions that the pharmacokinetics of $^{111}$In and $^{90}$Y labelled antibodies are the same as each other and the same in monkeys and humans. It was also assumed that there is no specific uptake or radiolabelled antibodies in the marrow so that the radioactivity in the blood and marrow are the same after a few (<5) hours. To generate numbers representative of humans, the following data for standard man were used: a total blood volume of 5000 ml; marrow spaces; absorbed fractions for $^{90}$Y beta-particles; and the thickness of the endosteal layer. Due to the high energy of the $^{90}$Y beta-particles, the radiation absorbed dose in the marrow and the endosteal layer are for all practical purposes the same.

Figure 11:
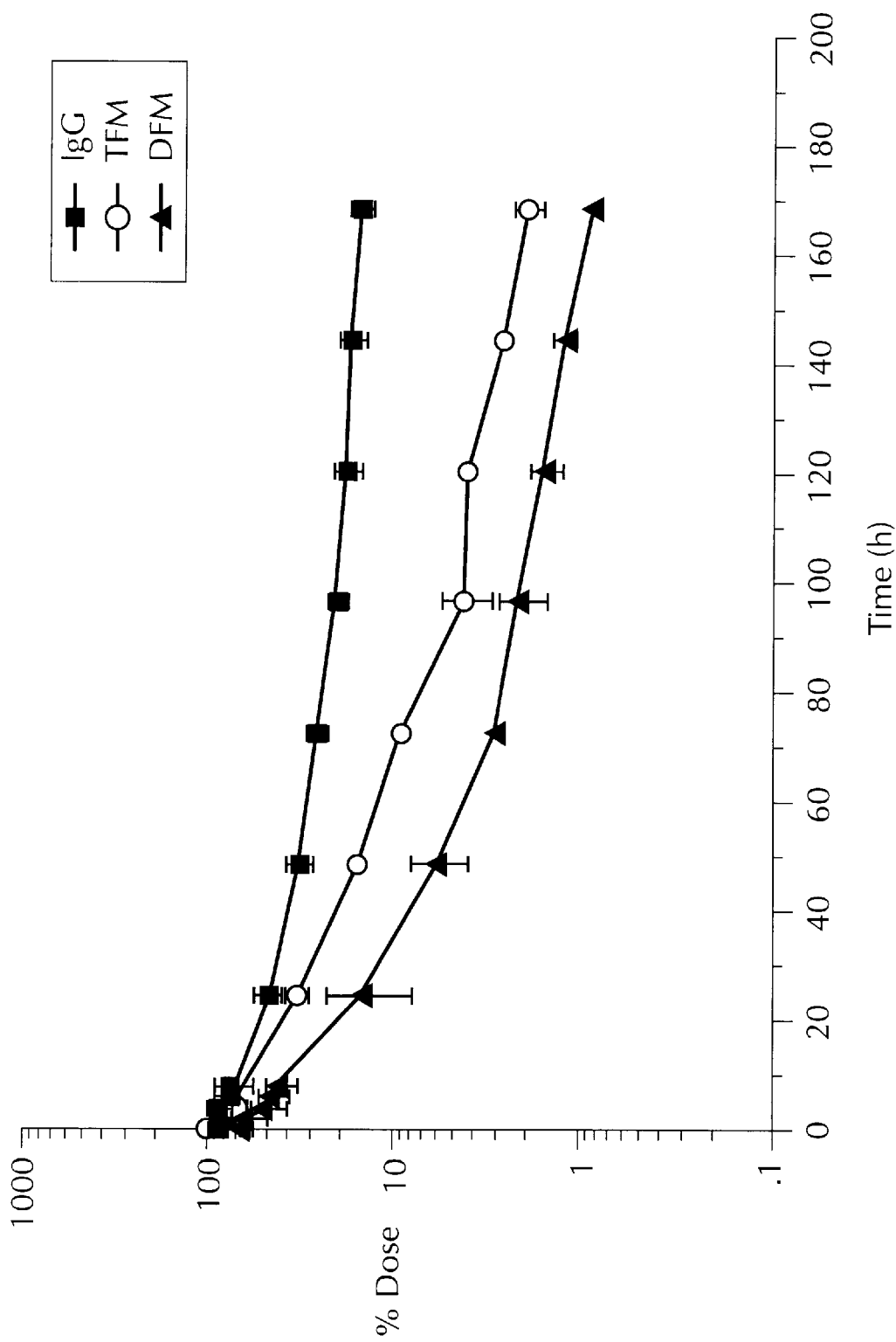
FIG. 11 shows pharmacokinetic profiles of $^{111}$In hA33 IgG, TFM™ and divalent Fab fragments (herafter "DFM™") in cynomolgus monkeys.

FIG. 11 represents the pharmacokinetic profiles of $^{111}$In hA33 IgG (■), TFM™ (○) and DFM™ (▲) in cynomolgus monkeys. Data was corrected for decay and plotted as mean percentage injected dose remaining at each time point. Due to safety considerations, these components were labelled with $^{111}$In rather than $^{90}$Y, since previous work suggested that $^{90}$Y-labelled IgG and fragments show pharmacokinetics and biodistribution very similar to those labelled with $^{111}$In. The plasma clearance profiles are shown in FIG. 11 with the alpha and beta phase half life values in Table 4.

TABLE 4

| Antibody Form | t1/2α (hours) | t1/2β (hours) |
|---|---|---|
| IgG | 15.8 | 129.0 |
| TFM ™ | 12.8 | 53.7 |
| DFM ™ | 10.8 | 42.0 |

As expected from pharmacokinetic data in ice and guinea pigs, both TFM™ and DFM™ cleared faster from the circulation than IgG. In addition, DFM™ cleared more quickly than TFM™. When plasma clearance was examined without decay correction for the isotope (Table 5) the data was most consistent with monophasic kinetics for IgG and TFM™ with biphasic kinetics for DFM™. Dosimetric calculations based on these data suggest that when labelled with $^{90}Y$ at equivalent amounts of radioactivity injected, the DFM™ gives approximately a five-fold lower absorbed dose to the bone marrow than IgG, while TFM™ gives a two-fold lower absorbed dose (Table 5).

TABLE 5

| Antibody Form | Effective half life (hours) | Absorbed dose to red marrow & endosteum (rads/mCl) |
|---|---|---|
| IgG | 40.5 | 12.0 |
| TFM ™ | 21.9 | 6.3 |
| DFM ™ | 4.7α/23.6β | 2.6 |

Single chain antibodies (SCA) can also be generated from mAb A33. Single chain antibodies are small in size, which allows for better diffusion into tumor tissues. They also have a short serum half-life, which reduces toxicity, for example, to the bone marrow. Lower tumor uptake may result from rapid SCA clearance from the blood. Single chain antibody SCA-A33 was produced. This antibody retains the binding specificity of mAb A33 and shows about 3-fold lower binding affinity than the intact mAb. SCA-A33, as well as other single chain antibodies, may be used therapeutically for local/regional perfusion via the hepatic artery for liver metastases and for primary lesions via superior mesenteric artery perfusion.

EXAMPLE IX

The prior examples show, inter alia, the efficacy of the murine form of mAb A33 in human therapy. The following experiments show that the humanized mAb, also described supra, is also therapeutically effective.

A study was carried out, using twelve patients. These were patients who had been diagnosed as having unresectable colorectal tumors (stage III or stage IV, using standard nomenclature), who had not responded to or failed standard chemotherapy and were not resistant to chemotherapy.

The subjects received humanized mAb A33, at doses of 10 mg/m$^2$, 25 ng/m$^2$, or 50 mg/m$^2$, in cycles of four weekly doses. Of the twelve subjects, one received only 20% of the first infusion, due to complications resulting from underlying hypertension which was exacerbated by the saline solution and human serum albumin in the infusions.

Given the reactivity of the humanized mAb with normal colon cells, attention was paid to whether the doses were leading to bowel toxicity. With the exception of two patients, who were receiving the highest dose, no significant toxicity was seen. Of the two patients mentioned supra, both developed transient grade 1–2 nausea and vomiting immediately after infusion. One of these patients also developed several episodes of nausea and vomiting. This patient also suffered from bowel obstruction, at time points not involved in the study reported herein. Following identification of the obstruction, the bowel loop identified as causing the obstruction was found, and resected. Obstructive symptoms were secondary to numerous adhesions identified in the patient, and were believed to be a result of radiation damage, but not the mAb therapy. The patient did, however, develop an immune response to the humanized mAb, and was taken off the study after six months of treatment. Her disease had stabilized.

The second patient showed a 40% reduction in serum carcino-embryonic antigen (CEA) levels, and metabolic disorders associated with tumor lysis syndrome (uric acid: 22 ug/dl). She also experienced shaking chills. Uric acid levels did not decrease significantly with hydration. Due to the patient's advanced colon cancer she was treated conservatively and died of progressive renal insufficiency.

All of the patients were monitored, frequently, for blood in their stools. Only one subject, treated at 25 mg/m$^2$, developed transient, positive guaiac tests. A colonoscopy did not detect a bleeding site, and random biopsies of colon mucosa showed no specific abnormalities. Subsequently, the patient's stools became guaiac negative, and have remained so. This patient's disease stabilized for 12 months, and she has had only a single positive guaiac test. The result of this aspect of the experiments is that a maximum toxic dose was not established.

A second feature of the experiments was simply to determine whether or not anti-tumor activity was observed. Indeed, it was found at all three dose levels. One patient, treated at 10 mg/m$^2$, had a reduction of serum CEA from 80 to 3.0 ng/ml, and had a partial response of lung, liver, and lymph node disease. Following more than 11 months of treatment, her serum CEA levels have been in the normal range for sixteen months. Two patients who received 25 mg/m$^2$ doses, had reductions in CEA levels of 25 and 40%, at 3 and greater than 10 months of therapy. Two patients at 50 mg/m$^2$ showed reduction in CEA levels of 40 and 20% respectively, and stabilization of disease (at 2 months–6 months of treatment). In summary, five of the eleven patients showed reductions in serum CEA levels.

The foregoing examples show, inter alia, that neoplasias can be treated via administration of humanized monoclonal antibody A33. The results disclosed herein were achieved with unlabelled humanized mAb A33, but it will be clear that labels, such as $^{133}I$, $^{125}I$, etc., may be used, as these were functional in an in vivo context for the murine mAb. Other labels with an anti-tumor effect may also be used.

The experiments show that A33 antigen is a target for immunotherapy using a humanized antibody. Hence, when humanized monoclonal antibody A33 is used herein, it refers to any humanized antibody, as well as any derivatives thereof, such as antibody fragments, oligomeric antibodies, and so forth, as long as these are also specific to the same target as is the humanized monoclonal antibody described herein.

Neoplasia as used herein refers to any abnormal growth of cells, as long as they present antigen A33 on their surface. Exemplary of this condition is colon cancer, including metastasized colon cancer. The amount of the humanized monoclonal antibody used to alleviate the neoplasia will vary, depending upon the severity of the condition, the overall health of the subject, and so forth. Generally, however, a dose of from about 5 mg/m$^2$ to about 100 mg/m$^2$, wherein the dose is administered once, or more than once in a given week, is preferred. Most preferred is a dose of from about 10 mg/m$^2$ to about 50 mg/m$^2$, administered once per week. Infusions of the humanized monoclonal antibody are preferred, but other forms of administration, such as intravenous or intraperitoneal administration are also contemplated, as are all standard modalities for administering anti-tumor agents.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for causing regression of a colorectal carcinoma or a gastric carcinoma in a subject in need thereof, comprising administering to said subject an amount of a $^{111}$In radiolabelled humanized monoclonal antibody or a $^{111}$In radiolabelled binding fragment of a humanized monoclonal antibody, said $^{111}$In radiolabelled humanized monoclonal antibody or $^{111}$In radiolabelled antigen binding fragment of said humanized monoclonal antibody binding to antigen A33 which is presented on surfaces of cells of said colorectal carcinoma or gastric carcinoma, and wherein said amount is effective for provoking regression of said colorectal carcinoma or said gastric carcinoma.

2. The method of claim 1, comprising administering said $^{111}$In radiolabelled humanized monoclonal antibody or said $^{111}$In radiolabelled antigen binding fragment of a humanized monoclonal antibody in a dose of from about 5 mg/m$^2$ to about 100 mg/m$^2$.

3. The method of claim 2, wherein said dose is from about 10 mg/m$^2$ to about 50 mg/m$^2$.

4. The method of claim 1, comprising administering said $^{111}$In radiolabelled humanized monoclonal antibody or radiolabelled antigen binding fragment of a humanized monoclonal antibody by infusion.

5. The method of claim 1, comprising administering said $^{111}$In radiolabelled humanized monoclonal antibody or said radiolabelled antigen binding fragment of a humanized monoclonal antibody intravenously or intraperitoneally.

6. The method of claim 1, wherein said colorectal cancer or gastric cancer has metastasized.

* * * * *

```
                              SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 108
        (B) TYPE: amino acid
        (C) STRANDEDNESS: single
        (D) TOPOLOGY: linear (ii) MOLECULE TYPE: <Unknown>
         (A) DESCRIPTION: SEQ ID NO: 1

(vi) ORIGINAL SOURCE:
         (A) ORGANISM: Mouse A33

(xi) SEQUENCE DESCRIPTION: SEQ ID NO: 1:

Asp Ile Val Met Thr Gln Ser Gln Lys Phe Met Ser Thr Ser Val Gly
                  5                  10                  15

Asp Arg Val Ser Ile Thr Cys Lys Ala Ser Gln Asn Val Arg Thr Val
                 20                  25                  30

Val Ala Trp Tyr Gln Gln Lys Pro Gly Gln Ser Pro Lys Thr Leu Ile
             35                  40                  45

Tyr Leu Ala Ser Asn Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Leu Gln His Trp Ser Tyr Pro Leu
                 85                  90                  95

Thr Phe Gly Ser Gly Thr Lys Leu Glu Val Lys Arg
                100                 105

(2) INFORMATION FOR SEQ ID NO: 2:

(i) SEQUENCE CHARACTERISTICS:
        (A) LENGTH: 108
        (B) TYPE: amino acid
        (C) STRANDEDNESS: single
        (D) TOPOLOGY: linear (ii) MOLECULE TYPE: <Unknown>
         (A) DESCRIPTION: SEQ ID NO: 2

(vi) ORIGINAL SOURCE:
         (A) ORGANISM: Human A33

(xi) SEQUENCE DESCRIPTION: SEQ ID NO: 2:

Asp Ile Gln Met Thr Gln Ser Pro Ser Ser Leu Ser Val Ser Val Gly
```

```
                 5                  10                 15
Asp Arg Val Thr Ile Thr Cys Lys Ala Ser Gln Asn Val Arg Thr Val
                    20                  25                  30

Val Ala Trp Tyr Gln Gln Lys Pro Gly Leu Ala Pro Lys Thr Leu Ile
            35                  40                  45

Tyr Leu Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Phe
65                  70                  75                  80

Glu Asp Ile Ala Thr Tyr Phe Cys Gln Gln His Trp Ser Tyr Pro Leu
                85                  90                  95

Thr Phe Gly Gln Gly Thr Lys Val Glu Val Lys Arg
                100                 105
```

(2) INFORMATION FOR SEQ ID NO: 3:

(i) SEQUENCE CHARACTERISTICS:
        (A) LENGTH: 117
        (B) TYPE: amino acid
        (C) STRANDEDNESS: single
        (D) TOPOLOGY: linear (ii) MOLECULE TYPE: <Unknown>
        (A) DESCRIPTION: SEQ ID NO: 3

(vi) ORIGINAL SOURCE:
        (A) ORGANISM: Mice A33

(xi) SEQUENCE DESCRIPTION: SEQ ID NO: 3:

```
Glu Val Lys Leu Val Glu Ser Gly Gly Gly Leu Val Lys Pro Gly Gly
                5                   10                  15

Ser Leu Lys Leu Ser Cys Ala Ala Ser Gly Phe Ala Phe Ser Thr Tyr
                    20                  25                  30

Asp Met Ser Trp Val Arg Gln Thr Pro Glu Lys Arg Leu Glu Trp Val
            35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Pro Thr Thr Val Val Pro Phe Ala Tyr Trp Gly Gln Gly Thr Leu
                100                 105                 110

Val Thr Val Ser Ala
        115
```

(2) INFORMATION FOR SEQ ID NO: 4:

(i) SEQUENCE CHARACTERISTICS:
        (A) LENGTH: 117
        (B) TYPE: amino acid
        (C) STRANDEDNESS: single
        (D) TOPOLOGY: linear (ii) MOLECULE TYPE: <Unknown>
        (A) DESCRIPTION: SEQ ID NO: 4

(vi) ORIGINAL SOURCE:
        (A) ORGANISM: Human A33

(xi) SEQUENCE DESCRIPTION: SEQ ID NO: 4:

Glu Val Gln Leu Leu Glu Ser Gly Gly Gly Leu Val Gln Pro Gly Gly

-continued

```
                5                   10                  15
Ser Leu Arg Leu Ser Cys Ala Ala Ser Gly Phe Ala Phe Ser Thr Tyr
            20              25              30

Asp Met Ser Trp Val Arg Gln Ala Pro Gly Lys Gly Leu Glu Trp Val
        35              40              45

Ala Thr Ile Ser Ser Gly Gly Ser Tyr Thr Tyr Tyr Leu Asp Ser Val
    50              55              60

Lys Gly Arg Phe Thr Ile Ser Arg Asp Ser Ser Lys Asn Thr Leu Tyr
65              70              75              80

Leu Gln Met Asn Ser Leu Gln Ala Glu Asp Ser Ala Ile Tyr Tyr Cys
                85              90              95

Ala Pro Thr Thr Val Val Pro Phe Ala Tyr Trp Gly Gln Gly Thr Leu
            100             105             110

Val Thr Val Ser Ser
            115
```